United States Patent [19]  [11] Patent Number: 4,923,620
Pall  [45] Date of Patent: May 8, 1990

[54] DEVICE FOR DEPLETION OF THE LEUKOCYTE CONTENT OF BLOOD AND BLOOD COMPONENTS

[75] Inventor: David B. Pall, Roslyn Estates, N.Y.

[73] Assignee: Pall Corporation, Glen Cove, N.Y.

[21] Appl. No.: 260,391

[22] Filed: Oct. 20, 1988

Related U.S. Application Data

[63] Continuation-in-part of Ser. No. 110,413, Oct. 20, 1987, abandoned, and a continuation-in-part of Ser. No. 218,169, Jul. 13, 1988, abandoned.

[51] Int. Cl.⁵ .............................................. B01D 35/02
[52] U.S. Cl. ................................... 210/767; 210/435; 210/445; 210/451; 210/456; 210/497.01
[58] Field of Search .............. 210/767, 435, 445, 451, 210/456, 497.01

[56] References Cited

U.S. PATENT DOCUMENTS

| | | | |
|---|---|---|---|
| 2,834,730 | 5/1953 | Painter et al. | 210/504 |
| 3,448,041 | 6/1969 | Swank | 210/446 |
| 3,593,854 | 7/1971 | Swank | 210/445 |
| 3,765,536 | 10/1973 | Rosenberg | 210/446 |
| 3,905,905 | 9/1975 | O'Leary et al. | 210/445 |
| 3,935,110 | 1/1976 | Schmid et al. | 210/456 |
| 3,935,111 | 1/1976 | Bentley | 210/446 |
| 3,954,621 | 5/1976 | Etani et al. | 210/314 |
| 4,009,714 | 3/1977 | Hammer . | |
| 4,009,715 | 3/1977 | Forberg et al. | 210/455 |
| 4,087,363 | 5/1978 | Rosemeyer et al. | 210/489 |
| 4,092,246 | 5/1978 | Kummer | 210/497.1 |
| 4,116,845 | 9/1978 | Swank | 210/446 |
| 4,157,967 | 6/1979 | Meyst et al. | 210/449 |
| 4,229,306 | 10/1980 | Hein et al. | 210/446 |
| 4,246,107 | 1/1981 | Takenaka et al. | 210/806 |
| 4,283,289 | 8/1981 | Meyst et al. | 210/448 |
| 4,294,594 | 10/1981 | Sloane, Jr. et al. | 210/497.01 |
| 4,330,410 | 5/1982 | Takenaka et al. | 210/767 |
| 4,370,381 | 1/1983 | Horikoshi et al. | 210/508 |
| 4,376,675 | 3/1983 | Perrotta | 162/145 |
| 4,416,777 | 11/1983 | Kuroda et al. | 210/446 |
| 4,422,939 | 12/1983 | Sharp et al. | 210/445 |
| 4,476,023 | 10/1984 | Horikoshi et al. | 210/446 |
| 4,477,575 | 10/1984 | Vogel et al. | 210/767 |
| 4,534,757 | 8/1985 | Geller | 604/85 |
| 4,608,173 | 8/1986 | Watanabe et al. | 210/502.1 |
| 4,617,124 | 10/1986 | Pall et al. | 210/508 |
| 4,618,533 | 10/1921 | Steuck | 428/315.7 |
| 4,636,312 | 6/1987 | Willis | 210/416.1 |

FOREIGN PATENT DOCUMENTS

| | | |
|---|---|---|
| 0045476 | 2/1982 | European Pat. Off. . |
| 0155003 | 9/1985 | European Pat. Off. . |
| 0267286 | 5/1988 | European Pat. Off. . |
| 2222951 | 7/1974 | Fed. Rep. of Germany . |
| 1575753 | 9/1980 | United Kingdom . |
| 2056301 | 3/1981 | United Kingdom . |

*Primary Examiner*—W. Gary Jones
*Attorney, Agent, or Firm*—Leydig, Voit & Mayer

[57] ABSTRACT

Devices for the depletion of leukocytes in blood products, preferably comprising an upstream porous element including means for removal of gels, at least one intermediate porous element including means for removal of microaggregates, and a downstream element including means for removal of leukocytes by both adsorption and filtration, preferably with at least one of the elements having been modified to a CWST in excess of 53 dynes/cm.

14 Claims, 2 Drawing Sheets

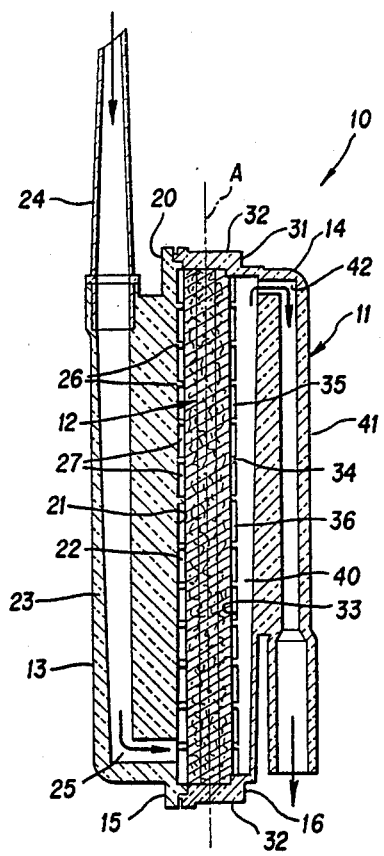
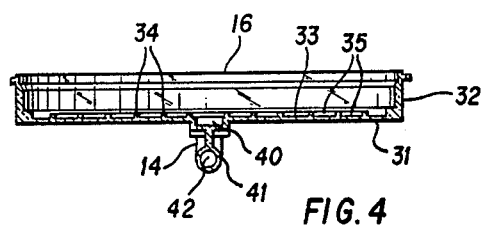

DEVICE FOR DEPLETION OF THE LEUKOCYTE CONTENT OF BLOOD AND BLOOD COMPONENTS

This application is a continuation-in-part of U.S. application Ser. No. 07/110,413 filed on Oct. 20, 1987, now abandoned, and a continuation-in-part of U.S. Application Ser. No. 07/218,169 filed on July 13, 1988, now abandoned, both of which are incorporated herein by reference.

TECHNICAL FIELD

This invention relates to a method for depleting the leukocyte content of whole blood and products derived therefrom, particularly from human packed red blood cells including cells which have been stored prior to transfusion for any period up to their allowable storage period, and a device for effecting that depletion.

BACKGROUND OF THE INVENTION

It has been the practice for 50 years or more to transfuse whole blood, and more recently blood components, from one or more donors to other persons. With the passage of time and accumulation of research and clinical data, transfusion practices have improved greatly. One aspect of current practice is that whole blood is rarely administered; rather, patients needing red blood cells are given packed red cells (hereinafter PRC), and patients needing platelets are given platelet concentrate. These components are separated from whole blood by centrifuging, the process providing, as a third product, plasma, from which various other useful components ar obtained.

In addition to the three above-listed components, whole blood contains white blood cells (known collectively as leukocytes) of various types, of which the most important are granulocytes and lymphocytes. White blood cells provide protection against bacterial and viral infection.

In the mid to late seventies, a number of investigators proposed that granulocytes be separated from donated blood and transfused into patients who lacked them, for example, those whose own cells had been overwhelmed by an infection. In the resulting investigations, it became apparent that this practice is generally harmful, since patients receiving such transfusion developed high fevers, had other adverse reactions, and generally rejected the transfused cells. Further, the transfusion of packed cells or whole blood containing donor leukocytes can be harmful to the recipient in other ways. Some of the viral diseases induced by transfusion therapy, e.g., Cytomegaloviral Inclusion Disease which is a life threatening infection to newborns and debilitated adults, are transmitted by the infusion of homologous leukocytes. Another life-threatening phenomenon affecting immunocompromised patients is Graft versus host disease (GVH); a disease in which the transfused leukocytes actually cause irreversible damage to the blood recipient's organs including the skin, gastrointestinal tract and neurological system. Conventional red cell transfusions have also been indicted as adversely influencing the survival of patients undergoing surgery for malignancy of the large intestine. It is believed that this adverse effect is mediated by the transfusion of agents other than donor red blood cells including the donor's leukocytes.

Removal of leukocytes to sufficiently low levels to prevent the undesired reactions, particularly in packed red cells including those which have been stored for relatively long periods of time, is an objective of this invention.

In the currently used centrifugal methods for separating blood into the three basic fractions (packed red cells, platelet concentrate, and plasma), the leukocytes are present in substantial quantities in both the packed red cells and platelet concentrate fractions. It is now generally accepted that it would be highly desirable to reduce the leukocyte concentration of these blood components to as low a level as possible. While there is no firm criterion, it is generally accepted that many of the undesirable effects of transfusion would be adequately reduced if the leukocyte content were reduced by a factor of about 100 or more prior to administration to the patient. This approximates reducing the total content of leukocytes in a single unit of PRC (the quantity of PRC obtained from a single blood donation) to less than $0.1 \times 10^9$.

Defining a Unit of Blood, and a Unit of Packed Red Cells

Blood banks in the United States commonly draw about 450 milliliters (ml) of blood from the donor into a bag which usually contains an anticoagulant to prevent the blood from clotting. Herein the quantity drawn during such a donation is defined as a unit of whole blood.

Whole blood is rarely used as such; instead most units are processed individually by centrifugation or by gravity settling to produce one unit of red cell concentrate in blood plasma, referred to herein as PRC (packed red cells). The volume of a unit of PRC varies considerably dependent on the hematocrit (percent by volume of red cells) of the drawn blood, which is usually in the range of 37% to 54%; and the hematocrit of the PRC, which usually is in the range from 70% to 80%. Most PRC units are in the range of 250 to 300 ml, but variation below and above these figures is not uncommon.

Drawn whole blood may alternatively be processed by separating the red cells from the plasma, and resuspending them in a physiological solution. A number of physiological solutions are in use. The red cells so processed may be stored for a longer period before use, and with some patients there may be some advantages in the removal of plasma. "Adsol" is the trade name of one such system. Similar products are used in Europe and other parts of the world.

As used herein the term "blood product" includes anti-coagulated whole blood, packed red cells obtained therefrom, and red cells separated from plasma and resuspended in physiological fluid.

In parts of the world other than the United States, blood banks and hospitals may draw less or more than about 450 ml of blood; herein, however, a "unit" is herein defined by the United States' practice, and a unit of PRC or of red cells in physiological fluid is the quantity derived from one unit of whole blood.

As used herein, PRC refers to the blood product described above, and to similar blood products obtained by other means and with similar properties.

Previously Available Means to Remove Leukocytes From PRC

The Spin-Filter system for obtaining leukocyte depleted packed red cells is described by Parravicini, Rebulla, Apuzzo, Wenz and Sirchia in Transfusion 1984; 24:508-510, and is compared with other methods by Wenz in CRC Critical Reviews in Clinical Laboratory Sciences 1986; 24:1-20. This method is convenient and relatively inexpensive to perform; it has been and continues to be used extensively. However, the efficiency of leukocyte removal, while generally 90% or better, is not sufficiently high to prevent adverse reactions in some patients.

Centrifugation methods are available which produce lower levels of leukocytes in red cells, but these are laboratory procedures which are very costly to operate, and sterility of the product is such that it must be used within 24 hours.

Other methods for leukocyte depletion, such as saline washing or deglycerolizing frozen red cells, have been or are used, but these have disadvantages for economical, high reliability service, and cannot be used at bedside.

A number of devices have been proposed in which fibers are packed into housings, and whole blood passed through them in order to remove microaggregates and a portion of the white cell content. These devices have all required saline to be applied either before or after use, or both before and after use. Further these devices have been poorly suited for use with PRC, in which they show early clogging and often or always fail to remove leukocytes to below $0.1 \times 10^9$ per unit of PRC or of whole blood. None are ideal for bedside use.

Characteristics Desirable in a Leukocyte Depletion Device

An ideal device for leukocyte depletion use would be inexpensive, relatively small, and be capable of delivering blood to the patient within about 30 seconds after connection to the bag of red cells and the patient's vein. The device should then deliver to the patient at least one unit (the product of a single blood donation) of red cells in which the leukocyte content has been reduced to a total of no greater than $1 \times 10^9$, and preferably to a level of less than $0.1 \times 10^9$. The capability of delivering a full second unit of packed red cells with maintenance of the high efficiency with respect to removal of leukocytes is also desirable. Further, because of the high cost and limited availability of red blood cells, this ideal device would deliver the highest possible proportion of the red cells originally present in the bag. The device would similarly be effective for blood products which have been stored for a relatively long period of time, including up to the date beyond which its useful life will have expired. Such a device is an object of this invention.

Devices which have previously been developed in attempts to meet this objective have been based on the use of packed fibers, and have generally been referred to as filters. However, it would appear that processes utilizing filtration based on separation by size cannot succeed for two reasons. First, the various types of leukocytes range from granulocytes and macrocytes, which can be larger than 15 micrometers, to lymphocytes, which are in the 5 to 7 micrometer and larger range. Together, granulocytes and lymphocytes represent the major proportion of all of the leukocytes in normal blood. Red blood cells are about 7 micrometers in diameter, i.e., in size between the two major components which must be removed. Secondly, all of these cells may deform so as to pass through much smaller openings than their normal size. Accordingly, and because it can be observed by microscopic examination that leukocytes are adsorbed on a variety of surfaces, it has been widely accepted that removal of leukocytes is accomplished by adsorption, rather than by filtration.

Attempts have been made to reduce leukocyte concentration in blood by exposure to a variety of surfaces, including polyamide, polyester, acrylics, cellulosics (e.g., cotton), cellulose acetate, and siliconized glass wool. Fibrous devices available to this date have at best been only partially successful, for the reasons described below. As the problems attendant on the earlier devices are reviewed, the manner in which the device and method in accordance with this invention are superior will become apparent.

Blood Component Recovery

In the preceding section, reference was made to the desirability of recovering a high proportion of the packed red cells delivered to the separation device. There are several causes for reduced recovery of red cells:

(a) Losses due to hold up within the connecting tubing and the drip chamber;

(b) Losses due to liquid which remains within the device itself at the conclusion of the transfusion; and (c) Losses due to adsorption on the surfaces of the device, or due to mechanical entrapment within the device.

(d) Loss due to clogging of the filter prior to completion of the passages of one or two units of blood.

Losses due to cause (a) can be minimized by use of a device which in bedside use requires only to have its inlet connected to the blood bag and its outlet to a drip chamber connected to the patient's vein, thus avoiding the use of side connections which are, for example, required if saline is used for priming. Losses can be further reduced if the design of the device is such as to permit use of a relatively small drip chamber. Losses due to cause (b) are referred to generally, and are reported herein, as "hold-up volume" measured in milliliters. Losses due to cause (c), if any, will be reported as due to adsorption. As for losses due to cause (d), one of the objectives of this invention is a device which does not clog, or which very rarely clogs, during the administration of two units of PRC even if the PRC is at or near its permissible storage life. More generally, an objective of this invention is a leukocyte depletion device having the highest possible red cell recovery.

Capacity

As separated from whole blood in current blood banking practice, packed red cells contain not only a proportion of the leukocytes present in the blood as drawn from the donor, but also some platelets (which tend to be very adhesive), fibrinogen, fibrin strands, tiny fat globules, and numerous other components normally present in small proportions. Also contained are factors added at the time the blood is drawn to prevent clotting, and nutrients which help to preserve the red cells during storage.

During the centrifuging process which concentrates the red cells and partially separates them from the remaining components, there is a tendency for microaggregates to form in PRC. These may comprise some red cells together with leukocytes, platelets, fibrinogen, fibrin, and other components. Gels, which may be formed by fibrinogen and/or fibrin, are frequently present in PRC produced by blood banks.

The gels are somewhat viscous, and though liquid, form a separate gelatinous phase in the blood plasma. Once segregated by filtration, gels may be identified in a spent filter by their tendency to cohere in stringy forms when manipulated under a microscope at 30 to 50 magnification.

Packed red cells can be refrigerated and stored for use within a period of 21 to 42 days or more depending on the additive system used. For CPDA-1 anticoagulated PRC, the permissible storage period in the U.S. is 35 days. During storage, the number and size of the microaggregates increase with time. Further, gel-like bodies generally form which may comprise fibrinogen, degenerated protein, and degenerated nucleic acids, and which often contain what appears on microscopic examination to be aggregates of leukocytes. Occasionally, small fat globules present in the blood when drawn may coalesce to form larger globules.

If the leukocyte depletion device comprises a porous structure, microaggregates, gels and occasionally fat globules tend to collect on or within the pores, causing blockage which inhibits flow.

In hospital practice, bedside transfusions usually use gravity, developing no more than 0.1 to 0.14 $kg/cm^2$ to induce flow from the storage bag through the leukocyte removal device to the patient. For this reason a particularly important characteristic of a separation device is its resistance to clogging.

Because of the unusual and highly variable combination of clogging factors, the experience of a person skilled in the art of filter design is inadequate when applied to removal of the undesirable components listed above from PRC, and novel, inventive approaches have been required to design an efficient prefilter, particularly when the PRC has been stored for a relatively long period of time.

The best of the devices on the market during the period of development of this invention was rated by its manufacturer to have a capacity for CPDA-1 anticoagulated PRC of one unit, with a blood hold-up volume of about 64 cc. The same device was rated for use with two units of blood product which had been freed of plasma by centrifuging and subsequently resuspended in a physiological solution. Predecessor devices by the same manufacturer had a blood product hold-up volume of about 52 cc; however, this device is no longer being marketed and was replaced by the larger device because of excessive frequency of clogging.

Devices in accordance with this invention can be designed to deliver any required number of units of PRC while maintaining an average removal efficiency greater than about 99.5%, preferably greater than about 99.9%. However, such a unit, for example, one rated to process four units of PRC, might have an internal volume such that as much as 30 to 50% of the red cells could be lost by hold-up within the device if it were employed to process a single unit of PRC. Most commonly, one or two PRC units are needed by a patient. Hence, a device sized to process a single unit of PRC with greater than 99.9% efficiency, but capable of passing a second unit while maintaining high efficiency, is seen to be a very useful and economical size, and has been selected as a primary objective of this invention. As discussed below, unless otherwise stated, it is this size of device (which will be referred to as an "adult" size) to which reference is being made.

While the devices described herein are principally directed to the primary objective described above, by proportionally changing the dimensions, equipment suitable for use with larger or smaller quantities of PRC can be made. A version of the device in accordance with this invention, designated as a "pediatric" size, with approximately one-half the area and hence one-half the capacity of the adult device, has been extensively used during development of this invention, for reasons of economy of whole blood and PRC used for testing, and because there is need for such a unit in hospital practice.

The microaggregates which cause clogging vary in size from about 200 micrometers down, and vary in quantity and size distribution with age, as well as randomly from one unit of packed red cells to the next. The gels vary with respect to both firmness and quantity. Large fat globules appear in a small but significant proportion of packed red cell specimens. Hematocrit (percent by volume of red cells) and viscosity can each vary over a wide range. This variability in characteristics makes the causes and onset of clogging extremely variable from one unit of blood to the next. Under these circumstances, while the development of a prefilter draws in part on science and on experience common to those familiar with the field of filtration, there is a large component of chance and intuition in the achievement of an effective prefilter.

The design of an efficient, small volume gel prefilter system which will contribute to the objective of achieving high efficiency of leukocyte removal while rarely or never clogging on one unit of packed red cells and which will pass all of two units in the great majority of cases, be it with newly drawn or with older blood, is an objective of this invention.

For an important class of patients, namely those such as thalassemics who are dependent on regularly repeated transfusions in order to maintain life, physicians recognize a special need for high efficiency leukocyte removal, and for the use of relatively fresh PRC. If transfused with PRC which is less than five days old, thalassemics require two or three units of PRC at 3 week intervals, however, if older PRC is used, transfusion at more frequent intervals is needed. Some physicians whose patient roster includes thalassemics will not use blood older than 5 days. For such applications the gel and microaggregate removal characteristics of the filter are less critical, and a filter can be designed to have a smaller hold up of PRC, and to be produced at less cost.

For the more general application in which a very significant proportion of the PRC is stored for more than 15 to 35 days or more prior to use, it is critical that the filter reliably deliver its stated capacity with a frequency near to 100% while maintaining high efficiency and low hold up. Failure to complete passage of a second unit is costly in terms of PRC lost, in the time of the nurse-technician and the physician, and can be harmful to the patient.

Accordingly, the products of this invention are directed to use with both fresh and older PRC.

Ease and Rapidity of Priming

Ease of use is an important characteristic of any leukocyte depletion system. As noted above, for leukocyte depletion devices, ease of priming is a particularly important factor. The term "priming" refers to start-up of flow of PRC from the bag through the filter to the drip chamber. An object of this invention is to keep that time to below about 30 seconds. A short priming period is always desirable to conserve nurse/technician time, but can be life saving when quick administration is required as, for example, when serious blood loss is unexpectedly experienced during surgery.

Preconditioning of Leukocyte Depletion Devices Prior to Priming

A number of devices in current use require pretreatment prior to passing blood, usually consisting of passing physiological saline, which may or may not be delivered to the patient's vein.

The necessity for such an operation is clearly very undesirable, for the reasons set out in the preceding section.

The reasons for using such pretreatment vary. They include removal of acid hydrolysate developed during steam sterilization of devices containing cellulose acetate fibers, assurance of freedom from foreign solids which may be present in natural fibers, and if the fibers are hygroscopic, to prevent hemolysis (loss of the integrity of red blood cells with subsequent loss of their contents to the external milieu).

An objective of this invention is a leukocyte depletion device which requires no preconditioning prior to bedside use.

Definition of Pore Diameter

Below 25 micrometers "pore diameter" is as determined by the modified OSU F2 test described in the section headed Examples. Above 25 micrometers, microscopic observation was used to estimate the approximate diameter of spherical particle which would be retained by a porous medium.

Definition of Element and of Integral Element

The word "element" as used above, and generally as used herein, denotes a portion of the overall assembly which consists of porous web in the form of one or more layers which may or may not be bonded to each other, but which performs a defined function within the filter assembly. Each of the layers is preformed, usually by hot compression, to controlled density and pore size, either as a single layer, or in combination with one or more other layers.

The expression "integral element" denotes a portion of the overall assembly which contains one or more layers of porous web, with (if there are more than one) the layers bonded to each other. An integral element is a unitary, complete structure having its own integrity, self-contained and independent of the other elements until assembled.

Wetting of Fibrous Media

When a liquid is brought into contact with the upstream surface of a porous medium and a small pressure differential is applied, flow into and through the porous medium may or may not occur. A condition in which no flow occurs is that in which the liquid does not wet the material of which the porous structure is made.

A series of liquids can be prepared, each with a surface tension of about 3 dynes/cm higher compared with the one preceding. A drop of each may then be placed on a porous surface and observed to determine whether it is absorbed quickly, or remains on the surface. For example, applying this technique to a 0.2 micrometer porous polytetrafluoroethylene (PTFE) filter sheet, instant wetting was observed for a liquid with a surface tension of 26 dynes/cm. However, the structure remained unwetted when a liquid with a surface tension of 29 dynes/cm was applied.

Similar behavior is observed for porous media made using other synthetic resins, with the wet-unwet values dependent principally on the surface characteristics of the material from which the porous medium is made, and secondarily, on the pore size characteristics of the porous medium. For example, fibrous polyester (specifically polybutylene terephthalate (hereinafter "PBT") sheets) which have pore diameters less than about twenty micrometers were wetted by a liquid with a surface tension of 50 dynes/cm, but were not wetted by a liquid with a surface tension of 54 dynes/cm.

In order to characterize this behavior of a porous medium, the term "critical wetting surface tension" (CWST) has been defined as described below. The CWST of a porous medium may be determined by individually applying to its surface, preferably dropwise, a series of liquids with surface tensions varying by 2 to 4 dynes/cm, and observing the absorption or non-absorption of each liquid. The CWST of a porous medium, in units of dynes/cm, is defined as the mean value of the surface tension of the liquid which is absorbed and that of a liquid of neighboring surface tension which is not absorbed. Thus, in the examples of the two preceding paragraphs, the CWST's were respectively 27.5 and 52 dynes/cm.

In measuring CWST, a series of standard liquids for testing are prepared with surface tensions varying in a sequential manner by 2 to 4 dynes/cm. Ten drops of each of at least two of the sequential surface tension standard liquids are independently placed on representative portions of the porous medium and allowed to stand for 10 minutes. Observation is made after 10 minutes. Wetting is defined as absorption into or obvious wetting of the porous medium by at least nine of the ten drops within 10 minutes. Non-wetting is defined by non-absorption or non-wetting of at least nine of the ten drops in 10 minutes. Testing is continued using liquids of successively higher or lower surface tension, until a pair has been identified, one wetting and one non-wetting, which are the most closely spaced in surface tension. The CWST is then within that range and, for convenience, the average of the two surface tensions is used as a single number to specify the CWST.

Appropriate solutions with varying surface tension can be prepared in a variety of ways, however, those used in the development of the product described herein were:

Wetting of Fibrous Media by Blood

In packed red cells, as well as in whole blood, the red cells are suspended in blood plasma, which has a surface tension of 73 dynes/cm. Hence, if packed red cells or whole blood is placed in contact with a porous medium, spontaneous wetting will occur if the porous medium has a CWST of 73 dynes/cm or higher.

Hematocrit is the percent by volume occupied by red cells. The hematocrit of packed red cells usually ranges from 70 to 80%. Thus, 70 to 80% of the volume of packed red cells consists of the red cells themselves and, for this reason, the surface characteristics of the red cells influence the wetting behavior of PRC. This is also true for whole blood, in which the normal hematocrit ranges from 37 to 54%. The surface tension of the red cell surfaces is given in the literature as 64.5 dynes/cm. ("Measurement of Surface Tensions of Blood Cells &

Proteins", by A.W. Neumann et al., from Annals N.Y.A.S., 1983, pp. 276–297.)

The benefits conferred by preconditioning fibers to CWST values higher than the natural CWST of synthetic fibers include:

(a) When priming for any reason is done using lower pressures than the 0.2 kg/cm$^2$ used in this study, for example by gravity, the time to achieve priming is significantly reduced. At 0.2 kg/cm$^2$, the reduction is, however, so small as to be difficult to measure.

(b) An important aspect of this invention is the discovery that fibrous media treated to convert the fiber surfaces to a particular range of CWST perform better with respect to time required for priming, efficiency and resistance to clogging than do fibrous media with CWST values outside of those ranges.

(c) Synthetic fiber media whose CWST values have been elevated by grafting have superior fiber to fiber bonding and are for this reason preferred for use in making the preformed elements used in this invention.

(d) Portions of unmodified filters may remain unwetted, thereby inhibiting flow through those areas.

(e) Devices made using unmodified synthetic fibers are recommended by their manufacturers to be flushed with saline prior to use. This operation is undesirable since it causes blood loss due to hold-up within the complex tubing arrangement required, adds to cost, operation time, and operation complexity, and increases the probability that sterility may be lost.

(f) Blood has been observed to clot when exposed to unmodified synthetic fibers.

DISCLOSURE OF THE INVENTION:

In accordance with the subject invention, a device and method for depleting the leukocyte content of a blood product is provided.

The subject invention provides a device for the depletion of the leukocyte content of a blood product comprising at least first, second, and third preformed porous elements with the second element interposed between the first and third elements, each successive element having a smaller pore diameter than that preceding it, the first element including means for removing gels, the second element including means for removing microaggregates, and the third element including means for removing leukocytes.

This first device can have a third element which has a pore diameter in the range from about 4 to about 8 micrometers. For example, the third element can have a pore diameter in the range from about 4 to about 5.5 micrometers, the first device then being well suited for processing a blood product having an age of about 2 to about 5 to 10 days, or the third element can have a pore diameter in the range from about 6 to about 8 micrometers, the first device then being well suited for processing a blood product having an age in excess of about 10 or 15 days.

The first device can have a first element which comprises a needled fibrous structure. The first element can be hot compressed to a controlled thickness. The average pore diameter of the first element can be such as to require, when prewetted by isopropyl alcohol, a differential pressure of 4 to 7 cm of water column to induce air flow through it at the rate of 0.5 cm/second through the first element.

The first device can include at least two interposed elements comprised of porous media which in at least three steps span in approximate geometric progression the pore diameter range from about 25 to about 10 micrometers.

The first device can include at least two interposed elements comprised of porous media which have progressively stepwise decreasing pore diameters spanning the range from about 25 to about 10 micrometers.

The first device can include a single interposed element in which the pore diameter varies stepwise from about 25 micrometers down to a pore diameter in the range from about 10 to about 15 micrometers.

The first device can include a surfactant which has been added to one or more of the elements. The surfactant can have characteristics which induce a surface tension in the range of about 55 to 45 dynes/cm in a blood product processed through it.

The first device can have at least one element which has been modified to a CWST in excess of 53 dynes/cm. For example, at least one of the elements can be modified to a CWST in excess of about 59 dynes/cm or at least one of the elements can be modified to a CWST in excess of 63 dynes/cm. Alternatively, at least one of the elements can be modified to a CWST in the range from about 55 to about 75 dynes/cm. For example, at least one of the elements can be modified to a CWST in the range from about 55 to about 75 dynes/cm. As a further alternative, at least one of the elements can be surface modified by exposure to an energy source while in contact with a monomer containing at least one hydroxyl moiety and one moiety capable of activation by an energy source, together with a monomer containing at least one hydrophobic moiety and one moiety capable of activation by an energy source.

The first device can include first, second, and third elements each having an effective cross-sectional area which is in excess of 54 square cm. Further, the total voids volume in all of the elements can be less than 28 milliliters. The total internal voids volume of the first device can be less than 37 milliliters.

The first device can have a third element in which the means for removing leukocytes includes a filtration means.

The subject invention also provides a device for the depletion of the leukocyte content of a blood product comprising at least first, second, and third porous elements with the second element interposed between the first and third elements, each successive element having a smaller pore diameter than that preceding it, the first element including means for removing gels, the second element including means for removing microaggregates, the third element including means for removing leukocytes, and at least one of the elements having been modified to a CWST in excess of 53 dynes/cm.

This second device can have all of the elements compressed to a controlled thickness prior to assembly.

The second device can consistently provide prior to clogging a capacity of at least two units of blood product of any age up to and including its permissible limit for human use. At least one of the component elements can be compressed to a controlled thickness prior to assembly. The total voids volume of all the elements can be less than 28 milliliters and the total internal voids volume of the second device can be less than 37 milliliters. The porous elements can be fibrous and the total surface area of all of the fibers can be less than 4 square meters. With the total surface area of all the fibers being less than 4 square meters, the pore diameter of the third element can be in the range of 4 to 8 micrometers. The total surface area of all the fibers alternatively can be less than 3.5 square meters. With the total surface area of all the fibers less than 3.5 square meters, the pore diameter of the third element can be in the range from about 4 to about 8 micrometers.

The second device can have at least one of the elements compressed to a controlled thickness prior to assembly.

Devices in accordance with this invention, including the first and second devices described above, can include a first element which has two or more means for removing gels.

The subject invention further provides a device for the depletion of the leukocyte content of a blood product comprising at least one integral element preformed of synthetic fibers, the surface of the fibers having a modified CWST in excess of 53 dynes/cm.

This third device can have synthetic fibers which have been surface modified to increase their CWST by 2 or more dynes/cm.

The third device can have a CWST in excess of 59 dynes/cm. For example, the CWST can be in excess of 63 dynes/cm.

The third device can have fibers which have been surface modified by exposure to an energy source while in contact with a monomer containing at least one hydroxyl moiety and one moiety capable of activation by an energy source, together with a monomer containing at least one hydrophobic moiety and one moiety capable of activation by an energy source.

The subject invention additionally provides a device for depletion of leukocytes from a blood product comprising at least one element in which a fibrous medium has been radiation grafted to obtain a critical wetting surface tension in excess of 53 dynes/cm and thereafter hot compressed to form a non-friable coherent body.

This fourth device can have the element modified to a CWST in the range of about 55 to 75 dynes/cm.

The fourth device can have the fibrous surface modified by exposure to an energy source while in contact with a monomer containing at least one hydroxyl moiety and one moiety capable of activation by an energy source, together with a monomer containing at least one hydrophobic moiety and one moiety capable of activation by an energy source.

The subject invention additionally provides a device for the depletion of the leukocyte content of a blood product comprising at least on integral, preformed element of synthetic fibers including means for removing leukocytes.

This fifth device can have the synthetic fibers modified to a CWST in the range of about 55 to 75 dynes/cm.

The fifth device can have the fibrous surface modified by exposure to an energy source while in contact with a monomer containing at least one hydroxyl moiety and one moiety capable of activation by an energy source, together with a monomer containing at least one hydrophobic moiety and one moiety capable of activation by an energy source.

The subject invention also provides a device for the depletion of the gel content of a liquid phase prior to filtration and thereby extending the capacity of a filter assembly, comprising at least first and second porous elements, the first element composed at least in part of a needled fibrous web and the second element having a smaller pore size than the first.

This sixth device can deplete the gel content of a liquid phase which is a blood product. The average pore diameter of the first element can be such as to require, when prewetted by isopropyl alcohol, a differential pressure of 4 to 7 cm of water column to induce flow of air through it at a rate of 0.5 cm/second through the first element. The effective flow path can comprise, in part, three or more elements preformed prior to assembly, each with cross-sectional flow area in excess of 54 square centimeters. The total voids volume of all the elements can be less than 28 milliliters and the total internal voids volume can be less than 37 milliliters.

The sixth device can have a second element which comprises at least one planar parallel non-woven component. A third element can be included with the second element disposed between the first and the third elements, at least one of the second and third elements being modified to a CWST within about 2 to 20 dynes/cm of the surface tension of the liquid phase. This consistently provides prior to clogging a capacity of at least two units of a blood product of any age up to and including its permissible limit for human use. The total voids volume of all the elements can be less than 28 milliliters and the total voids volume of the device can be less than 37 milliliters. At least one of the second and third elements can be modified to a CWST in the range of about 55 to about 75 dynes/cm.

The sixth device can have at least one of the component elements compressed to a controlled thickness prior to assembly. For example, all of the component elements can be compressed to a controlled thickness prior to assembly.

The sixth device can include a second element which has been surface modified by exposure to an energy source while in contact with a monomer containing at least one hydroxyl moiety and one moiety capable of activation by an energy source, together with a monomer containing at least one hydrophobic moiety and a moiety capable of activation by an energy source.

The subject invention also provides a device for the depletion of the leukocyte content of a blood product comprising a housing including an inlet and an outlet and defining a fluid flow path between the inlet and the outlet, an upstream porous element, at least one intermediate porous element, and a downstream porous element, the upstream element including means for removing gels, the intermediate element including means for removing microaggregate, and the downstream element including means for removing leukocytes, the upstream, intermediate, and downstream elements being secured within the housing by an interference fit.

The subject invention additionally provides a device for separating one or more substances for a fluid to be administered to a patient, the device comprising a housing including an inlet and an outlet and defining a fluid flow path between the inlet and the outlet and a separating element disposed within the housing across the fluid flowpath and including a downstream surface, wherein the inlet communicates with the housing near the bottom of the housing and upstream from the separating element and wherein the housing further includes passage means for allowing air in the fluid to separate from the fluid, the passage means being disposed downstream from the separating element and communicating with the outlet near the top of the housing.

This eighth device can have a housing which includes a wall facing the downstream surface of the separating element and defining a plenum and can include a passage means having a slot disposed in the wall and communicating between the plenum and the outlet, the slot being deeper than the plenum. The wall can include a plurality of concentric circular grooves which communicate with the slot. The slot can extend from the bottom to the top of the housing and the depth of the slot can increase from the bottom to the top of the housing. The slot length can be from 50 to 80% of the inner diameter of the housing, and the slot can extend to the top of the housing. The slot depth can increase towards the top of the housing. The housing can have a generally circular configuration and the slot can extend from the top of the housing along at least a portion of the vertical inner diameter of the housing.

The subject invention provides a device for separating one or more substances from a fluid to be administered to a patient, the device comprising a generally housing including an inlet and an outlet and defining a fluid flow path between the inlet and the outlet and a disc shaped separation element disposed within the housing and having upstream and downstream surfaces, wherein the housing further includes an inlet section facing the upstream surface of the separating element and defining an inlet plenum, the inlet including a ridge extending vertically along the exterior of the inlet section and a passageway which opens at the top of the inlet ridge, extends through the inlet ridge, and communicates with the inlet plenum at the bottom of the housing, and an outlet section facing the downstream surface of the separating element and defining an outlet plenum and including a slot which is deeper than the outlet plenum and which communicates between the outlet plenum and the outlet, the outlet including a ridge extending vertically along the exterior of the outlet section and a passageway which opens at the bottom of the outlet ridge, extends through the outlet ridge, and communicates with the slot near the top of the housing.

This ninth device can include an inlet section having a plurality of concentric circular grooves and an access extending between the inlet passageway and each circular groove, the circular grooves and the access collectively defining the inlet plenum and the inlet plenum having a depth which is greatest at the bottom of the housing near the inlet passageway.

The ninth device can include an outlet section having a plurality of concentric circular grooves which communicate with the slot, the slot extending from near the bottom of the housing to the top of the housing and having a greater depth at the top of the housing than at the bottom.

The ninth device can have a housing which further includes a cylindrical collar disposed about the periphery of the disc shaped separation element, the disc shaped separation element being sealed to the cylindrical collar by an interference fit between them.

The present invention further provides a method for the depletion of the leukocyte content of a blood product, for the depletion of the gel content of a liquid phase, or for separating one or more substances from a fluid to be administered to a patient, comprising passing the blood product, liquid phase, or fluid through the appropriate devices described above.

The present invention also provides a method for the depletion of the gel content of a liquid comprising passing the liquid through a needled fibrous web. A preferred liquid and such a method is a blood product, particularly PRC.

The present invention additionally provides a method for determining the wetting characteristic of a porous medium comprising applying at least one or more drops of each of at least two different liquids having different but closely spaced surface tensions to different locations on the porous medium and if necessary repeating this process until, of two liquids with neighboring surface tension, one is absorbed into the medium, and the other is not.

Significant and novel features of this invention which contribute to achieving high efficiency and capacity for leukocyte removal, and minimize loss of blood within the apparatus include:

(a) Previously disclosed devices have used relatively small cross sectional area perpendicular to the flow path, and as a consequence the liquid flow path through the filter medium is relatively longer. The preferred devices in accordance with this invention are larger in cross sectional area perpendicular to the flow path and correspondingly the flow path through the filter medium is shorter. The larger filter area at the upstream surface so obtained helps to prevent clogging by PRC or blood containing relatively large quantities of gels and microaggregates.

(b) In order to make the larger cross sectional area economic and practical and to obtain the required degree of prefiltration, each of the porous components of the preferred device in accordance with this invention is preformed prior to assembly to closely controlled dimension and density to form in whole or in part an integral element, self-contained and independent of other elements until assembled into a device in accordance with the subject invention.

Due to the pressure developed by the packing in devices utilizing packed fibers, devices used hitherto have had smaller cross-section and greater depth than the products of this invention. Preforming eliminates the pressure on the inlet and outlet faces of the housing which are inherent in a packed fiber system, preforming also permits one element, for example, the first stage prefilter of the assembled device, to be more or less compressible, yet have a lower or higher density than the one following it. This arrangement contributes to longer life in service.

By permitting the use of thinner walled injection molded housings, preforming makes it more practical to use larger cross sectional area leukocyte depletion devices which have longer life in service, coupled with at least equal and usually better leukocyte removal efficiency, equal or better red cell recovery, and less hold up, when compared with devices that use fibers or fibrous webs packed into a housing at assemblY. Preforming also contributes greatly to reduction of the internal volume of the filter assembly, thus reducing blood loss due to hold-up within the filter assembly, to higher removal efficiency, and to the ability to process a larger volume of PRC prior to clogging.

Devices have been disclosed and some made which incorporate various commercially made woven and non-woven media as prefilters along with a more finely pored last stage consisting of fibrous mats, all packed within a plastic housing. These devices have not had the efficient prefiltration and filtration made possible by preforming. None of them have used preformed elements, nor have they used any means equal in result to hot preforming, which achieves efficient pore diameters at higher densities, hence for equal results occupies less volume and holds up less blood. This is reflected in the comparative performance of the device now marketed which comes closest to matching the products of this invention; that device uses melt blown fibrous web readily identifiable as being in the form in which it comes off the machine, hence not preformed by any method. That product, compared with the product of this invention, has about twice the hold-up volume, has significantly lower efficiency, and in the United States is rated to pass only one unit of PRC, compared with two.

(c) The preformed element located in the upstream position of the assembly of preformed fibrous elements, hereinafter referred to as the "gel prefilter", has as its principal function the removal of gels which are present in a substantial proportion of the PRC units supplied by the blood banks. The extraordinarily effective gel prefilter makes possible the use of devices with a smaller internal volume, with less blood loss due to internal hold-up.

While the gel content of any specific unit of PRC is difficult to quantify, it is nevertheless readily apparent to one familiar with the art that PRC which has been stored more than 10 to 15 days, contains substantially more gels than does PRC stored for less than 5 days. As the gel content increases, so must the volume of the gel prefilter provided to remove and contain the gels. In this invention, we have provided two types of gel prefilter, one comprising a single layer for use with relatively fresh PRC, and a second comprising two or more layers for use with older PRC. Filter assemblies fitted with the single layer when used with fresh PRC will always deliver one unit of PRC, and only rarely fail to deliver a second unit prior to clogging. The multi-layer gel prefilter performs similarly for older blood near to or at its out-date limit. These gel prefilters constitute an important aspect of this invention.

(d) While the gel prefilter is extremely efficient in removing gels with a very small increase in pressure drop, and removes as well microaggregates which frequently are present suspended in the gels, it removes at best only a small portion of the microaggregates which are not contained within the gels.

Removal of these freely suspended microaggregates is accomplished by one, two, or more layers of prefiltration using filter media of successively smaller pore diameter, and these are followed by a layer whose primary purpose is to remove leukocytes, sometimes denoted herein as the "adsorption element". The resulting fluid delivered to the downstream element is substantially free of gels and microaggregates and has been partially freed of leukocytes.

(e) A surprising discovery was that the downstream (adsorption, or for brevity, "last") element removes leukocytes from the suspension by two mechanisms, both operating simultaneously. One mechanism is by adsorption of leukocytes to the fibrous surfaces; the second is by filtration. The first mechanisms cited is effective by virtue of the quantity of fiber surface. The second mechanism depends principally upon maintaining the pore diameter of the filter medium within or below a specific range.

(f) Modification of the fiber surfaces, to promote easy wetting by the PRC. Priming of the filter, i.e., inducing flow of PRC through it, is more complex and more difficult than would appear at first sight.

If the CWST of the fiber surface is too low, for example that of unmodified synthetic fiber, relatively higher pressure is required to force the PRC to flow through. More seriously, areas of the filter medium tend to remain unwetted, preventing flow of PRC. Further, clotting may occur, especially with finer, high surface area fibers and with older blood.

For reasons which are not well understood, some filters which have CWST in excess of about 90 dynes/cm have been observed to have longer priming times. Since there appears to be no theoretical reason for the CWST of the filter media to greatly exceed the surface tension of water (73 dynes/cm) it appears advisable that the CWST be held within a range somewhat above the CWST of untreated polyester fiber (52 dynes/cm), and below about 75 dynes/cm. Nevertheless, filters with CWST in the range up to and over 90 dynes/cm and above have functioned well.

(g) The housing into which the element assembly is sealed is uniquely designed to achieve convenience of use, rapid priming, and efficient air clearance, this last leading to improved efficiency, longer service life, and further reduction in hold-up of PRC.

(h) The lateral dimensions of the elements are larger than the corresponding inner dimensions of the housing into which they are assembled. For example, if the elements are of disc form, the disc outside diameter is made 0.1 to 1% larger than the housing inside diameter. This provides very effective sealing by forming an interference fit with no loss of effective area of the elements, and contributes further towards minimization of the blood hold-up volume of the assembly, compared with a compression seal around the periphery of the filter element assembly, which blocks flow in the compressed area.

BRIEF DESCRIPTION OF THE DRAWINGS:

FIG. 1 is a cross sectional view of an exemplary depletion device embodying the present invention.

FIG. 4 is a cross sectional view of the outlet section shown in FIG. 3.

Figure 2:
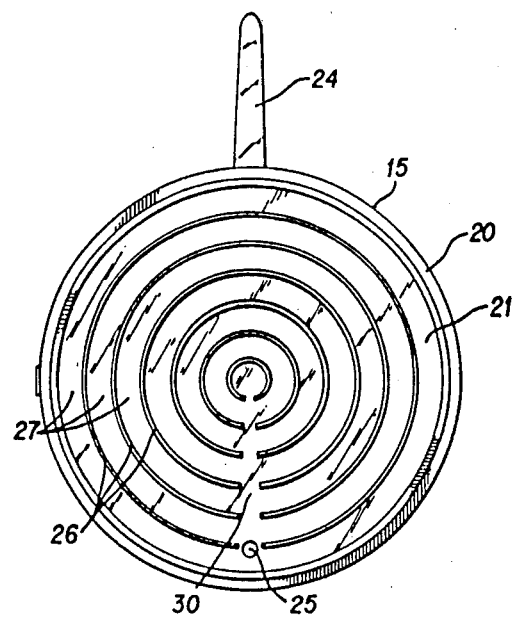
FIG. 2 is an elevation view of the inside surface of the inlet section of the depletion device shown in FIG. 1.
Figure 3:
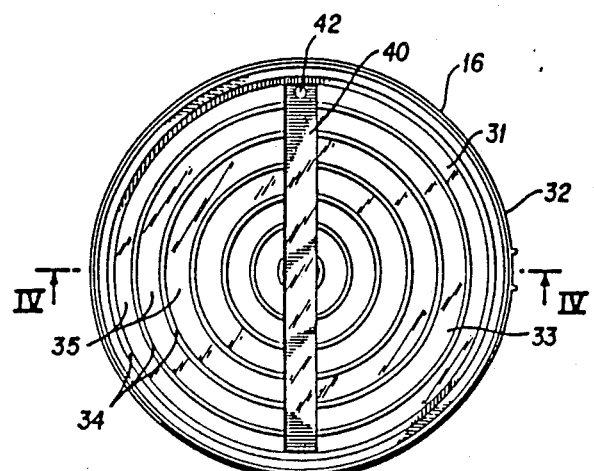
FIG. 3 is an elevation view of the inside surface of the outlet section of the depletion device shown in FIG. 1.

BEST MODE FOR CARRYING OUT THE INVENTION:

Material for Use in Construction of Leukocyte Removal Devices

A variety of starting materials other than fibers can be considered; for example, porous media could be cast from resin solution to make porous membranes, or sintered powder media could be used. However, considerations of cost, convenience, flexibility, and ease of fabrication and control, point to fibers as a preferred starting material In order to achieve good priming with the fibrous medium fully wetted and in the absence of surfactant deliberately added to reduce the surface tension of the blood product, it would appear at first glance from elementary consideration of the physical chemistry involved that blood component devices should be made of materials which have CWST values about equal to the surface tension of water, for example in the range of 70 to 75 dynes/cm or higher. Practical considerations dictate the use of commercially available fibers. Synthetic resins from which fibers are prepared commercially include polyvinylidene fluoride, polyethylene, polypropylene, cellulose acetate, Nylon 6 and 66, polyester, polyacrylonitrile, and polyaramid. An important characteristic of resins is their critical surface tension (Zisman, "Contact angles, wettability and adhesion", *Adv. Chem. Ser.* 43, 1–51, 1964). These resins have critical surface tensions ($\gamma_c$) ranging from less than 25 up to 45 dynes/cm. Experience has shown that the CWST of filter media in the pore size range needed for the products of this invention can be expected to be less than about 10 dynes/cm higher than the $\gamma_c$ value of the solid plastic. For example, for polytetrafluoroethylene, $\gamma_c$ is 18 and CWST is 27.5, while for a polyester PBT fibrous mat, $\gamma_c$ is 45, and CWST is 52. No suitable commercially available synthetic fiber has been found which has a CWST higher than about 52 dynes/cm.

In U.S. bedside transfusion practice, PRC is administered at a rate such that two units are infused over 1.5 to 4 hours. We have observed that when an unmodified melt blown polyester is used as a filter, clotting of the PRC can occur within a 2 to 3 hour period, completely blocking the filter.

Some natural fibers have CWST greater than 52, but natural fibers smaller than about 15 micrometers in diameter are not generally commercially available. Synthetic fiber webs which are less than about 5 micrometers in diameter can be made by the melt blowing process, and compared with natural fibers, such fibers require one third or less the mass to provide equal fiber surface area for adsorption of leukocytes, and consequently, occupy less volume when fabricated into filters of a given pore diameter. For this reason, natural fibers are not well suited for manufacturing leukocyte removal devices with optimally low hold-up volume. For example, a commercially available packed cotton fiber device currently used for leukocyte depletion has a priming volume of over 75 ml, which is more than twice the volume of the preferred adult device described in this application. Furthermore, the makers of this device require saline to be passed before and after the PRC has been passed, and the device is not suitable for bedside use. Additionally, blood so processed must be used within 24 hours.

The art of surface grafting has been the subject of extensive research for 25 years or more. Numerous publications in the scientific literature and a large number of patents describe a variety of methods and procedures for accomplishing surface modification by this means. One such method employs a variety of monomers comprising an acrylic moiety together with a second group which can be selected to vary from hydrophilic (e.g., —COOH or —OH) to hydrophobic (e.g., saturated chains such as —$CH_2CH_2CH_3$), and these have been used in the process of this invention. Heat, UV, and other reaction energizing methods can be used to initiate and complete the reaction. However, cobalt source radiation grafting has been selected as most convenient and has been used in this invention to modify the CWST of fibrous mats. By cut and try selection, mixtures of monomers or single monomers can be found which will produce a fibrous mat of polybutylene terephthalate in which the CWST has been increased from 52 to any desired value up to as high as is possible to be measured by the method described above. The upper limit is set by the paucity of liquids with surface tensions at room temperature higher than about 110 dynes/cm.

During the development of this invention, devices were prepared using media in which grafting was accomplished by compounds containing an ethylenically unsaturated group, such as an acrylic moiety combined with a hydroxyl group (for example, 2-hydroxyethyl methacrylate, or "HEMA"). A second acrylic monomer, such as methyl acrylate (MA) or methyl methacrylate (MMA), which tend to cause the grafted porous webs to have lower CWST, can be used in combination with HEMA, and by varying the proportions, any CWST between 35 to 45 to over 110 dynes per cm can be obtained. The devices so made are distinguished from devices prepared using components treated with surfactants, in that surfactants are removed by liquid passing through the device, whereas the alteration of surface characteristics obtained by grafting is permanent, and is not removed or altered by any amount of liquid passing through the device nor are the physical properties of the liquid altered, and in particular the surface tension is not altered.

Liquids with surface tensions lower than the CWST of the porous medium will wet the medium and, if the medium has through pores, will flow through it readily. Liquids with surface tensions higher than the CWST will not flow at all at low differential pressures, but will do so if the pressure is raised sufficiently. If the surface tension of the liquid is only slightly above the CWST, the required pressure will be small. Conversely, if the differential between the CWST and the surface tension of the liquid is high, the pressure required to induce flow will be higher.

It has been discovered that, when a liquid is forced under pressure to pass through a fibrous mat which has a CWST 15 to 20 dynes/cm lower than the liquid's surface tension, flow tends to occur in a non-uniform fashion, such that some areas of the mat remain dry. This is highly undesirable in a leukocyte depletion device, first because the pressure drop is higher causing earlier clogging, second because all the flow passes through only a portion of the available area, again increasing the probability of clogging, and third because only a portion of the fiber surface area available for adsorption of or retention by filtration of leukocytes is used for that purpose and, as a result, leukocyte removal is less efficient.

Solutions to the Problems of Poor Wetting of Synthetic Fibers and Consequent Slow Priming Fiber surface characteristics can be modified by a number of methods, for example, by chemical reaction including wet or dry oxidation, by coating the surface by depositing a polymer thereon, and by grafting reactions which are activated by exposure to an energy source such as heat, a Van der Graff generator, ultraviolet light, or to various other forms of radiation, among which $\gamma$-radiation is particularly useful.

As examples of these various methods, stainless steel fibers can be made water wettable, i.e., provided with a $\gamma_c$ greater than 72 dynes/cm by oxidation in air at about 370° C. to produce a thin oxide surface skin. Synthetic organic and glass fibers may be coated by polymers which contain at or near one end a reactive (e.g., epoxide) moiety and at the other a hydrophilic group. While the above methods and others known to those familiar with surface modification techniques can be used, radiation grafting, when carried out under appropriate conditions, has the advantage that considerable flexibility is available in the kinds of surfaces that can be modified, in the wide range of reactants available for modification, and in the systems available for activating the required reaction. In the subject invention $\gamma$-radiation grafting has been focused on because of the ability to prepare synthetic organic fibrous media with CWST over the full range of from 50 to well above 75 dynes/cm. The products are very stable, have undetectably low aqueous extractables levels and, in addition, improved adhesion between fibers is obtained when used in preformed prefiltration or adsorption elements.

Alternative means for coping with the poor wetting characteristics of synthetic fibers include changing the surface tension of the plasma in which the red cells are suspended, or changing the surface characteristics of the red cells. This can be accomplished, for example, by providing in the leukocyte depletion device a surfactant or a soluble material which reduces the surface tension of the red cell suspension.

The gel prefilter element used in preparing test devices for examples 1–106 was impregnated with a solution of a non-ionic surfactant which induced a surface tension of 48.5 to 51.5 dynes/cm in PRC flowing through it. Examples 107 et seq were performed using no surfactant.

Selection of Fiber Diameter for Use in Leukocyte Depletion Devices

As noted in the section headed "Characteristics Desirable in a Leukocyte Depletion Device", adsorption of leukocytes on fiber surfaces is widely accepted as the mechanism of leukocyte removal. Since the surface area of a given weight of fibers is inversely proportional to the diameter of the fibers, and removal of leukocytes by adsorption to the fiber surfaces is a significant mechanism for leukocyte depletion, it is to be expected that finer fibers will have higher capacity and that the quantity, as measured by weight of fibers necessary to achieve a desired efficiency, will be less if the fibers used are smaller in diameter.

For this reason, the trend has been to use finer fibers for leukocyte depletion. Historically, as the technology required to produce smaller diameter fibers has advanced, they have soon thereafter been packed into housings and/or proposed to be used for leukocyte depletion.

Selection of Fiber Material for Use in Leukocyte Depletion Devices

A number of commonly used fibers, including polyester, polyamides, and acrylics, lend themselves to radiation grafting, because they have adequate resistance to degradation by γ-radiation at the levels required for grafting, and they contain groups with which available monomers can react during or after irradiation.

As noted above, fiber diameters should be as small as possible. Synthetic fibers made by conventional spinneret extrusion and drawing are not currently available smaller than about 6 micrometers in diameter.

Melt blowing, in which molten resin is attenuated into fibers by a high velocity stream of gas and collected as a non-woven web, came into production in the 1960's and 1970's and has been gradually extended over the years with respect to the lower limit of fiber diameter with which webs could be made. Within recent years, webs with fiber diameters less than three micrometers have been achieved, and more recently, webs of good quality with average fiber diameter less than two micrometers have been made.

Some resins are better adapted to melt blowing of fine fibers than are others. Resins which work well include polypropylene, polymethylpentene, Nylon 6, polyester PET (polyethylene terephthalate), and polyester PBT (polybutylene terephthalate). Others that have not yet been tested may be found. Of the above listed resins, polyester PBT is a preferred material because it also lends itself to radiation grafting and to subsequent conversion into preformed elements of controlled pore size by hot pressing.

Polyester PBT has been the principal resin used for the development of the products of this invention and is, except for the gel prefilter, the resin used in the examples. It should be noted, however, that other resins may be found which can be fiberized and collected as mats or webs with fibers as small as 1.5 micrometers in diameter or less, and that such products, with their CWST adjusted if necessary to the optimum range, may be well suited to the fabrication of equally efficient but still smaller leukocyte depletion devices. Similarly, glass fibers, appropriately treated, may make possible devices with very low hold-up of blood.

The critical surface tension ($\gamma_c$) of PBT has been reported to be 45 dynes/cm and its CWST in the form of a fine fibrous mat has been measured as 52 dynes/cm.

Use of Needled Web in the Gel Prefilters

Non-woven webs are formed by a variety of means. The fibers may be suspended in air as they are extruded from molten plastic, and collected from air suspension on a moving belt or drum while still in a softened state or after the fibers have hardened. In another system the fibers are extruded and drawn as continuous filaments, which are then cut or torn to lengths of about 2 to 6 cm, followed by suspension in air and collection on a moving belt or drum. The surface on which the fibers collect is moving in the machine direction, generally at speeds of about 10 to 1000 meters/minute; as a consequence of this linear motion, the fibers within the web tend to be oriented more or less parallel to each other, and quite generally also parallel to the plane of the web; they may thus be classified as "planar parallel".

"Needled" webs, also known as "needle punched" webs are made by further processing a planar-parallel web by passing it through a machine fitted with a large number of rapidly reciprocating multiply barbed needles, which randomly engage fibers and pull or push them through the thickness of the web, causing fibers from one face to be pulled to the opposite face, where they become entangled with fibers at that face.

Multiple water jets have also been used to accomplish interlacing of fibers throughout the thickness of the web and the product of these (and other methods if they exist or may be developed) will be referred to hereinafter as having been "needled".

Needled webs are lofty, as they are made with very low density (often ranging in voids volume from about 95 to about 99%), and are relatively thick (often over about 3 to 5 millimeters). Their structure when examined by microscopy gives the appearance of an assembly of random diameter coils, many of which are oriented with the coil axis parallel to the plane of the web, and may be seen to offer easy access into the internal portion of the web for blood gels, which tend to be globular in form. This structure is in strong contrast with the orientation of a planar parallel non-woven web in which the fibers are parallel to the plane of the web, and which tend, even when quite coarse, to retain globular gels at or near the surface of the web.

Thus, blood gels appear to be readily able to enter into the very open surface of the coils of a needled non-woven while entry into a non-woven with fibers oriented parallel to the web is more difficult. It further appears that once gels have entered a needled web, they tend to be efficiently retained by smaller pores, which may be readily seen microscopically to be present. In effect, the curly fibrous structure allows easy entry and good retention, while structures comprising relatively straight fibers do not provide easy entry, and hence clog rapidly as gels collect at their upstream surface.

As gel laden blood flows through a needled filter medium, smaller pores are randomly encountered, and these are sufficient in number to have the net effect of collecting all or nearly all of the gels within the medium. This occurs with a very small increase in pressure drop, since the larger pores remain open to provide free passage for flow of the red cells suspended in plasma.

Whether or not these concepts of the filtration mechanism are valid, it has been found experimentally that the needled non-wovens are peculiarly (and unexpectedly) effective in allowing entry of gels and in then retaining them, while permitting blood or PRC to flow through them with a very small or negligible pressure drop increase.

In the course of the development of this invention, and prior to the first use of needled web in the examples of this invention, hundreds of tests were run with the objective of achieving consistently passage of two units of PRC with blood hold-up volume comparable with that of the examples. These tests used as many as 15 or more separate layers of medium, with stepped pore sizes varying in 7 to 10 steps from over 50 micrometers down to 5 to 10 micrometers. These tests used planar parallel non-woven media, and none were successful.

The use of needled webs made possible the development of the filters of this invention, which are capable of consistently processing older blood with high efficiency, without clogging and a hold-up volume of less than 30 to 35 cc.

While means other than needling may exist, or may be developed in the future, which produce media which on microscopic examination are similar to the needled media used in this invention, it should by understood that products made using such media fall within the scope of this invention.

A wide range of fibers, fiber combinations, and/or binders can be used to form the punched web. Any of these may be used if (a) they are amenable to subsequent controlled compaction by hot compression or by other means and (b) they are made using materials and under conditions appropriate for use in a device for processing human blood.

The webs used in the gel prefilters in the examples of this invention were formed using needle punched fibers with a non-ionic lubricant-finish (Freudenberg Non-Woven Ltd. Partners grade P14 of nominal weight 80 grams per square meter), in consequence of which a surface tension of 48 dynes/cm was measured when a 32 cm$^2$ disc was immersed into 300 ml of demineralized water. When gel prefilters prepared from such fibers were used to process PRC, the surface tension of the plasma of the PRC effluent from the device was reduced from about 73 dynes/cm to 48.5 to 51.5 dynes/cm. Similar surface tension data were obtained with other surfactants including ICI's Tween 80, BASF - Wyandotte's Pluronic L101 and Pluronic F68, all of which are physiologically acceptable for use in parenterals. Prior to use in examples 107 et seq the surfactant present in the needle punched medium was removed by detergent washing and water rinsing.

The Microaggregate Element

The principal function of the element following the gel prefilter is removal of microaggregates. A subsidiary function is removal by adsorption of a portion of the leukocytes.

For these purposes it preferably combines two, three or more layers of melt blown web. The layers constituting this element can be preformed separately and located adjacent to each other, or they can be preformed to a single element, or they can be combined with the adsorption element to form a single integral element.

The Adsorption Element

The principal function of this element is to provide the largest portion of the fiber surface on which leukocytes are removed by adsorption. It is most conveniently fabricated by preforming a number of layers of relatively smaller diameter fibrous web to form an integral element, or as noted above, it may be combined with the microaggregate element to form a single integral element comprising the adsorption element and the microaggregate element.

Filter Adsorber Assembly

A "filter-adsorber assembly" is obtained when a gel prefilter is assembled in the correct order with a microaggregate element and an adsorption element. All of the components may be separately preformed, or they may be formed to integral subassemblies in any convenient combination.

Description of an Exemplary Depletion Device

As shown in FIGS. 1–4, an exemplary depletion device 10 generally comprises a housing 11 and a filter-adsorber assembly 12. The housing 11 has an inlet 13 and an outlet 14 and defines a fluid flowpath between the inlet 13 and the outlet 14. The filter-adsorber assembly 12 is disposed within the housing 11 across the fluid flowpath and serves to separate undesirable substances, such as gels, fat globules, aggregates, and leukocytes, from a fluid, such as a suspension of packed red cells, flowing through the housing 11.

Two sizes of depletion devices have been tested, differing only with respect to the area through which the packed red cell suspension is passed. The smaller, defined as the pediatric size, has an effective area of 32 cm$^2$, and the larger, defined as the adult size, has an effective area of 62 cm$^2$. In both, disc-shaped filter-adsorber assemblies 12 are accommodated in cylindrical housings.

Housings can be designed to accept a variety of shapes of filter-adsorber assemblies. One such is, for example, a square. Those and other possible forms would in principle all be functional, provided that adequate flow area is provided.

A square filter-adsorber assembly would in theory allow more economical use of material, but would be less reliable if an interference fit seal is used in the manner described below for housings fitted with disc shaped filter-adsorber assemblies. If sealing is obtained by edge compression about the periphery, significant effective area is lost at the seal. For those reasons, cylindrical housings with disc shaped filter-adsorber assemblies assembled with an interference fit seal are preferred, although other forms may be used. Circular housings with an effective cross sectional area of 32 and 62 cm$^2$ have been used in developing this invention.

Housings can be fabricated from any suitably impervious material, including an impervious thermoplastic material. For example, the housing may preferably be fabricated from a transparent or translucent polymer, such as an acrylic or polycarbonate resin, by injection molding. Not only is such a housing easily and economically fabricated, but it also allows observation of the passage of the fluid through the housing. The housings are designed to withstand normal abuse during service, as well as internal pressures up to about 3 psi (0.2 kg/cm$^2$). This permits light construction, which is a desirable feature of this invention made possible by the use of preformed filter-adsorber assemblies. The force required to compress the fibers of an efficiently designed filter-adsorber assembly by packing of fibers into a housing is as high as 68 kilograms for a 62 cm$^2$ disc, or about 1.1 kg/cm$^2$, requiring heavier, bulkier, and more costly housing construction.

While the housing may be fashioned in a variety of configurations, the housing 11 of the exemplary separation device 10 is preferably fashioned in two sections, i.e., an inlet section 15 and an outlet section 16. The inlet section 15 includes a circular inlet plate 20, and the inside surface of the circular inlet plate 20 defines a wall 21 which faces the upstream surface of the filter-adsorber assembly 12.

The inlet 13 delivers the fluid to an inlet plenum 22 between the wall 21 and the upstream surface of the filter-adsorber assembly 12. In accordance with one aspect of the invention, the inlet 13 delivers the fluid to the inlet plenum 22 at or near the bottom of the housing 11, as shown in FIGS. 1 and 2.

The inlet may be variously configured. However, the inlet 13 of the exemplary separation device 10 includes a longitudinal inlet ridge 23. The inlet ridge 23 extends along the outside surface of the circular inlet plate 20 parallel to a diametrical axis A of the housing 11, which, in use, is positioned with the diametrical axis A oriented generally vertically. The upper end of the inlet ridge 23 may be fashioned as a socket for receiving a hollow spike 24 which is used to pierce the bottom of a bag containing the fluid, e.g., a blood bag. The inlet 13 further includes an inlet passageway 25 which opens at the upper end of the hollow spike 24, extends through the hollow spike 24 and the inlet ridge 23, and communicates with the inlet plenum 22 at the bottom of the inlet section 15.

The wall 21 of the circular inlet plate 20 includes a plurality of generally concentric circular ridges 26 which define concentric circular grooves 27. The ridges 26 abut the upstream surface of the filter-adsorber assembly 12. As shown in FIG. 2, the ridges 26 terminate in the lower portion of the inlet section 15, defining a passageway or access 30. The access 30 extends between the inlet passageway 25 and each circular groove 27, allowing fluid to flow from the inlet passageway 25 to the circular grooves 27. Collectively, the circular grooves 27 and the access 30 define the inlet plenum 22, which distributes the fluid delivered by the inlet passageway 25 over the whole upstream surface of the filter-adsorber assembly 12. To prevent aggregates and other large obstructions from blocking flow at or near the junction of the inlet passageway 25 and the inlet plenum 22 and, at the same time, to minimize hold-up volume in the housing 11, the depth of the inlet plenum 22 is greatest at the bottom of the housing 11 and decreases along the vertical axis A to a minimum value at the horizontal centerline of the housing 11.

The outlet section 16 of the housing 11 includes a circular outlet plate 31 and a cylindrical collar 32 which extends from the periphery of the circular outlet plate 31 to the periphery of the circular inlet plate 20. The cylindrical collar 32 is preferably integrally formed with the circular outlet plate 31 and joined to the circular inlet plate 20 in any suitable manner, e.g., by an adhesive or by sonic welding.

The inside surface of the circular outlet plate 31 defines a wall 33 which faces the downstream surface of the filter-adsorber assembly 12. The wall 33 includes a plurality of generally concentric circular ridges 34 which define concentric circular grooves 35. The ridges 34 abut the downstream surface of the filter-adsorber assembly 12. The circular grooves 35 collectively define an outlet plenum 36 which collects the fluid passing through the filter-adsorber assembly 12. The depth of the outlet plenum 36 is made as small as possible to minimize hold-up volume within the housing 11 without unduly restricting fluid flow.

In accordance with another aspect of the invention, the wall 33 further includes a passageway such as a slot 40 which communicates with the outlet 14 at or near the top of the outlet section 16. The slot 40, which collects fluid from each of the circular grooves 35 and channels the fluid to the outlet 14, preferably extends from the bottom to the top of the outlet section 16 along the vertical axis A. In the exemplary separation device 10, the width of the slot 40 remains constant but the depth of the slot 40, which is greater than the depth of the outlet plenum 36, increases from the bottom to the top of the outlet section 16 along the vertical axis A. Alternatively, the height may be less than the diameter of the housing, the width may vary, or the depth may remain constant. For example, the slot may extend from the top of the housing along the vertical axis A a distance in the range from about 80% of the inside diameter of the housing.

The outlet 14 may be variously configured. However, the outlet 14 of the exemplary depletion device 10 includes a longitudinal outlet ridge 41 which extends along the outside surface of the outlet plate 31 parallel to the vertical axis A. The lower end of the outlet ridge 41 may be fashioned as a tubing connector or as a socket for receiving a tubing connector or other apparatus. The outlet 14 further includes an outlet passageway 42 which communicates with the slot 40 at or near the top of the housing 11, extends through the outlet ridge 41, and opens at the lower end of the outlet ridge 41.

As blood starts to flow through the apparatus, filling it from the bottom and emptying at the top, air is displaced and flows towards and out of outlet passageway 42. By careful design of the exemplary apparatus it has been possible to reduce, but not to eliminate completely, the situation in which some liquid reaches the area 43 adjacent to the outlet passageway 42 before all of the air is cleared from the inner parts of the housing assembly. In the absence of slot 40, this lagging air flow would carry some red cell-containing suspension into the outlet . tube 42. Slot 40 allows the blood so carried to flow into the slot, where the air is harmlessly separated from the liquid suspension. The air then rises harmlessly to the outlet 14 ahead of the rising fluid level in the slot 40 and is almost completely ejected before the liquid level reaches the top of the outlet plenum 36 and outlet passageway 42. Thus, air is very efficiently cleared from the housing 11 of the exemplary depletion device 10 according to the invention. For example, in a depletion device which has an inside diameter of 8.9 centimeters, an initial air volume of 36 cc, and a slot 8 centimeters high, 0.73 centimeters wide, 0.2 centimeters deep at the bottom, and 0.33 centimeters deep at the top, the residual volume of air passing through the outlet after 1 or 2 cc of blood has passed through the outlet is estimated to be less than 0.1 cc.

In order to understand the importance of the slot and the flow passage configuration, the equivalent operation of a conventional leukocyte depletion unit will be described.

In conventional units, fluid enters at the top of the housing and exits at the bottom. The housing of such a unit is typically connected by plastic tubing between a blood bag upstream from the conventional housing and a transparent drip chamber downstream from the conventional housing and thence to the patient. During priming, the housing along with the drip chamber is inverted and blood is forced through the conventional housing into the drip chamber. This has the disadvantage that some pressure head is lost, but, more seriously, fluid reaches the exit of the conventional housing and enters the drip chamber while as much as 1 to 2 cc or more of air is still trapped in the conventional housing. When 3 to 4 cc of fluid has been collected in the drip chamber, it and the housing are returned to their normal position, leaving a reservoir of fluid in the bottom of the drip chamber and an air space above the fluid reservoir.

The transparent drip chamber performs a service in permitting observation of the droplet rate through the air space, thus providing guidance for flow regulation. It also performs a second service in that lagging air entering from the conventional housing is prevented from reaching the patient. Instead, the lagging air displaces an equivalent volume of fluid in the reservoir of the drip chamber. However, the reservoir must be large enough to ensure that the lagging air never totally displaces the fluid. Otherwise, the air may enter the vein of the patient.

Systems which permit a significant volume of air, e.g., 1 to 2 cc, to reach the drip chamber after it has been returned to its normal position, tend to do so non-reproducibly. Thus, the larger the volume of lagging air, the larger the volume of fluid which must be collected in the reservoir of the drip chamber. At the end of the administration, much of that volume is left in the drip chamber and, hence, is wasted. Because many of the fluids administered to a patient, e.g., fluids containing blood components such as red cells, are often difficult to obtain and exceedingly expensive, wasted fluid can be very costly. By maximizing air clearance and thereby allowing the use of a smaller reservoir in the drip chamber, the depletion device according to the present invention significantly reduces the amount of fluid wasted during administration.

The filter-adsorber assembly 12 preferably comprises a number of individually preformed layers as described below under the heading Fabrication of Fibrous Elements. During the development stage, housings were constructed for testing which incorporated the basic internal configuration described above, but in addition were variable with respect to the thickness of the filter-adsorber assembly. In this way, it was possible to test filter-adsorber assemblies varying in total thickness. In each case, the distance between the tips of the ridges 26, 34 of the inlet and outlet sections was adjusted to be equal to the nominal total thickness of the filter-adsorber assembly.

To provide an interference fit of the filter-adsorber assembly 12 within the housing 11, the filter-adsorber elements were cut from large precompressed slabs to a diameter 0.1 to 1% larger than the inside diameter of the cylindrical collar 32. The filter-adsorber elements were cut in such a manner as to maintain true right cylindrical form at their outer edges. This, coupled with the slight oversizing, provides good edge sealing, i.e., an interference fit, between the outer edges of the filter-adsorber assembly 12, made up of the various filter-adsorber elements, and the inner periphery of the housing 11, with 100% utilization of the full area and volume of the filter-adsorber assembly 12, thereby minimizing hold-up volume.

The edge sealing obtained by the interference fit has been shown on its own to be adequate, however, the importance of providing high reliability in production units is such that an auxiliary seal may be considered desirable. Such a seal can comprise a pair of inwardly facing flanges 1 to 1.5 millimeters wide, dimensioned such as to compress the filter medium between these peripheral flanges by 20 to 60%. Assemblies with and without this auxiliary seal have been used in the development of this invention.

Fabrication of Fibrous Elements

The fibrous elements which are assembled into the above described housings comprise a number of discrete individual elements, each of which performs one or more functions. In a preferred configuration of the leukocyte depletion device of this invention, and in the order in which the fluid flows, these layers comprise:

1. A first element is referred to as the gel prefilter. A high proportion of whole blood and PRC specimens contain gels, which very effectively clog filter media. These gels form a phase distinct from, and not miscible with, the blood plasma in which they are suspended, and visually are seen to have higher viscosity. The state-of-the-art procedure for coping with clogging of filters is enlargement of the pores of the upstream face of the filter, followed by successively varying smaller pores, continuously or in steps, but this procedure for reasons not fully understood was ineffective when applied prior to the development of the gel prefilter of this invention.

We have discovered that a very effective gel removal filter can be made by using as a starting material nonwoven web made by the needle punching process, with average fiber diameter between 10 to 40 micrometers, preferably between 15 and 30 micrometers, and more preferably between 20 and 25 micrometers. Needled webs are made using a number of multiple barbed needles, with the barbs oriented both upward and downward, which cause the fibers to assume the form of irregular loops, circles, and spirals, interspersed with a variety of other irregular shapes. In general, a majority of the fibers have the form of irregular shapes, with very few straight sections. Gels appear to penetrate easily into this type of web, and to be effectively retained within the web, as may be seen by post-test microscopic examination.

Needled webs with these characteristics are generally made thicker than desired for gel removal, and for optimal results must be compressed to a controlled smaller thickness. Fabric so made was discovered to be not only particularly effective in retaining gels, but to do so while occupying relatively little space within the filter housing. The smaller housing achieved in this manner holds up less blood, reducing PRC loss by about 50% compared with filters fitted with conventional prefiltration.

While the gel prefilter does not recover microaggregates directly by filtration, the gels it retains frequently contain a substantial number of microaggregates in a wide range of sizes, and these are efficiently retained along with the gels.

The gel prefilter is made with low density in order to have very high voids volume, and when made with fibers smaller than 30 to 50 micrometers in diameter, it is easily compressible. Webs made using fibers much less than 10 to 20 micrometers may tend to be excessively compressible, to the point where a few inches of pressure head during blood flow could cause a web partially filled with gels to be compressed, thereby reducing its pore diameter to an inefficient range. If made with fibers much above 30 to 50 micrometers, performance for gel removal deteriorates because the open area at equal pore size is smaller compared with webs made using finer fibers.

Preferred materials for making the gel prefilters are polyethylene terephthalate (PET) and polybutylene terephthalate (PBT). The PET web has been used in the form of 23 micrometer average fiber diameter web at a weight of 7 to 9 mg/cm$^2$, while the latter (PBT web) was a melt blown web with a filter diameter of 20 micrometers and with a weight/cm$^2$ of about 8 mg.

As purchased the PET medium has had too low a density, and the pore diameter was larger than desired. In order to remedy this, the webs were hot compressed to smaller thickness. As the webs are very compressible, control of thickness was established using a means of measurement denoted as the "fall-out test", as follows:

A 6.41 cm diameter disc is held in the jaws of a vernier caliper, with the jaws oriented vertically downward. The jaws are then slowly opened. The vernier setting at which the disc falls is the "fall-out" thickness of the disc.

For examples 1–106, a single layer of PET medium was used with the surfactant-lubricant on the fiber retained. This was hot compressed using the fall-out test to a value of 0.18 to 0.22 cm. A clearance of 0.9 mm was allotted at assembly into the filter housing. Examples 107–168 were similar except that the surfactant had been removed prior to hot compression.

Examples 169 et seq were made using:

(a) Upstream, one layer of PET hot compressed to a nominal fall-out value of 0.075 cm.

(b) Downstream, in the order noted, one layer of PET together with a layer of PBT medium, the two hot compressed together to form an integral layer with a nominal fall-out value of 0.10 cm.

(c) At assembly into the filter housing the space allotted to the assembly of (a) and (b) was 0.15 cm.

2. The second element is the microaggregate removal element, whose function is to remove aggregates which form particularly in older PRC.

Preferred material for making this element is melt blown PBT web.

For use except as noted in examples 1–168, this element comprised the following, listed in the order of flow:

A preformed layer made using three layers of web of average fiber diameter respectively 15, 10 and 7 micrometers.

A single preformed layer of 4.5 micrometer average fiber diameter web.

A single preformed layer of 4.5 micrometer average fiber diameter web of density in excess of the preceding layer.

As used in examples 169 et seq, the microaggregate removal elements comprised the following, listed in order of flow:

A first, second, and third layer respectively of average fiber diameter 3.5, 3.0 and 2.6 micrometers, hot compressed at assembly with the adsorption element described below, to make an integral element. Density after compression is lower compared with examples 1–168.

3. The third (adsorption) element has as its primary function the removal of leukocytes, primarily by adsorption and secondarily by filtration.

For examples 1–168, this element was prepared using multiple layers of 2.6 or 4.5 micrometer fiber, integrally bonded by hot compression. For examples 169 et seq this element was made using four layers of 2.4 micrometer fibrous web bonded together with the microaggregate removal layers to form an integral assembly of the seven layers.

The values cited above and in the examples can be varied within limits while meeting the objective of this invention. To determine whether any particular variation produces a fully equivalent product, tests are required. Thus, it should be understood that, while the precise fiber diameters, weights, densities, thicknesses and number of layers can be varied somewhat while achieving equivalent or possibly even better results, that which is disclosed herein is intended as a guide to the design of a device meeting the stated objectives of this invention and that devices made with such variations fall within the scope of this invention.

With the exception of the gel prefilter, all of the elements are preferably surface treated to a CWST in excess of about 55 dynes/cm, but not in excess of 75 to 80 dynes/cm.

Grafting Improves Adhesion During Hot Compression

Hot compressed element preforms made using melt blown fibrous mats which have been surface modified to raise their CWST values by 5 or more dynes/cm are palpably better with respect to firmness and resistance to fraying when compared with discs made by hot compression followed by radiation grafting. Grafting prior to hot compression is for this reason preferred; however, serviceable elements could be made by hot compression followed by grafting.

While the examples of this invention have used hot compression to form the integral elements which together combine to provide prefiltration, gel removal, and adsorption, it would be feasible to form the integral elements by other means, such as resin bonding, and a device utilizing this or similar alternatives is within the scope of this invention.

Melt blown fibers have been preferred for use in all but the first layer of these devices. Should finer melt blown or other fine fibers, for example, fibers made by mechanical fibrillation of larger diameter fibers, become available in the future, their use in elements for leukocyte depletion devices would be within the scope of this invention.

Edge Sealing the Preformed Elements into the Housing

The housing is preferred to be of generally disc form, or more rigorously stated, in part have the form of a right cylindrical element. The preformed elements are made also in right cylindrical form, of dimension 0.1 to 1% larger than that of the inner surface of the housing. When assembled, a good seal is obtained, with no detectable bypassing during service.

CWST of the Elements

The gel prefilter (first) element may have a low CWST without harm, and, indeed, may function better in that condition. The results of tests in which sufficient PRC is run through a device to cause clogging or near clogging, followed by dissection, inspection, and testing of the pressure drops of the individual layers, indicate that little, if any, improvement can be accomplished by increasing the CWST of this layer. The microaggregate filter and the adsorption section are preferably modified to a CWST of between 55 to 80 dynes/cm, and more preferably to between 59 and 73 dynes/cm, and still more preferably to between 62 and 68 dynes/cm.

Red Cell Recovery

No significant changes in hematocrit were detected when the hematocrit values for the PRC in the bag were compared with the effluent from the devices in accordance with this invention.

Some of the incoming blood or PRC is lost due to hold-up within the depletion device. That loss is reported as hold-up volume.

Characterization of Porous Media by Physical Characteristics

Formulae have been proposed to predict pore diameter. These formulae typically use fiber diameter, bulk (apparent) density; and fiber density. One such, for example, calculates the average distance between fibers. However, the average distance between fibers cannot be a meaningful predictor of performance as in any liquid flow path it is the largest pore or pores encountered which control performances, and this is particularly true of deformable "particles" such as leukocytes. In a fibrous mat such as made by melt blowing, the fibers are parallel to the plane of the surface, but are otherwise laid down in a random manner, and the pore size distribution is quite wide. Other means for forming fibrous mats, e.g., air laying, or formation on a Fourdrinier screen, also produce wide pore size distributions. In these circumstances, the average distance between fibers is clearly a poor predictor of performance. A variety of other formulae have been proposed to allow calculation of pore diameters from data on fiber diameter, fiber density and bulk density, but in over forty years of devising means to make and apply filter media, this applicant has never found any formula useful for calculating a priori the effective pore diameter of filters for liquid service.

Measurement of fiber surface area, for example by gas adsorption—popularly referred to as "BET" measurement— is a useful technique, as the surface area is a direct indication of the extent of fiber surface available to remove leukocytes by adsorption. The surface area of melt blown PBT webs can be used to calculate average fiber diameter:

$$\text{Total volume of fiber in 1 gram} = \frac{1}{1.38} \text{ cc}$$

(where 1.38 = fiber density of *PBT*, g/cc)

$$\text{hence } \frac{\pi d^2 L}{4} = \frac{1}{1.38} \quad (1)$$

$$\text{Area of the fiber is } \pi dL = A_f \quad (2)$$

$$\text{Dividing (1) by (2), } \frac{d}{4} = \frac{1}{1.38 A_f}$$

$$\text{and } d = \frac{4}{1.38 A_f} = \frac{2.9}{A_f}, \text{ or } (0.345 A_f)^{-1}$$

where L=total length of fiber per gram, d=average fiber diameter in centimeters, and $A_f$=fiber surface area in cm$^2$/g.

If the units of d are micrometers, the units of $A_f$ become M$^2$/g (square meters/gram) which will be used hereinafter.

A second characteristic necessary to describe a porous medium adequately to permit it to be reproduced is its pore diameter (Dp). We have used a modified OSU-F2 test for this purpose; this test and its mode of use are described in the following section, under the heading Examples.

Other characteristics which describe a porous medium include apparent (bulk) density ($\rho$) in grams/cubic centimeter (g/cc), the fiber density (also in g/cc), the thickness (t) of the elements of the medium, specified in centimeters (cm), the cross sectional area available for flow through the filtering element ($A_c$) in square centimeters (cm$^2$) [32 or 62 cm$^2$ for all the examples], and the CWST in dynes/cm. Specifying these parameters defines a filter of filter-adsorber element of predictable behavior when used for leukocyte depletion:

(a) $A_f$, the fiber surface area per gram, when multiplied by the weight ($A_c \times t \times \rho$) of the filter, is the fiber surface area available within the filter for removal of leukocytes by adsorption.

(b) An objective of this invention is a filter which will pass two units of PRC without clogging. Insofar as the cross sectional area $A_c$ is increased, the rate of flow per unit area is decreased, hence there is less tendency for clogging.

(c) Dp and t define the efficiency with which leukocytes are removed by filtration.

A fibrous filter-adsorber element for leukocyte depletion is defined by specifying the density of the fibers from which it is made, as well as $A_c$, $A_f$, Dp, $\rho$, t, and its CWST for each component or sub-assembly of components.

We have discovered that, in a fibrous leukocyte depletion filter, removal of leukocytes is accomplished partly by adsorption and partly by filtration. An important aspect of this invention is that by carefully defining and controlling Dp, and providing prefiltration in a novel but well defined manner, a filter can be achieved which has substantially lower volume when compared with a filter principally dependent on adsorption. This reduces the volume of PRC or blood hold-up, with important economy of PRC use, while at the same time providing higher efficiency and better capacity compared with the best similar devices hitherto available.

Whereas previously available devices depended nearly completely or largely on adsorption, and were relatively larger, the devices of this invention, using Dp as a basic design guide, depend comparatively substantially more on filtration, and as a result are smaller.

The following examples are offered by way of illustration.

EXAMPLES

The PRC and whole blood used in these examples were obtained from blood banks which conform to American Association of Blood Banks standards. Those using CPDA-1 anticoagulant were from the Greater N.Y. Blood Program in Melville, N.Y., and red cells suspended in physiological fluid using the Adsol anticoagulant system were obtained from the American Red Cross Blood Services, Rochester Region in Rochester, N.Y. Unless otherwise noted, the tests of the examples were run with PRC.

No blood product, including PRC, could be obtained from the blood bank in less than 2 days after it was drawn, as this was the minimum period required to test for the presence of infectious agents.

All leukocyte counts were made by conventional chamber counts, by well-trained technicians, and data reported is the average of at least two counts by different technicians. When testing adult size devices, two bags of PRC or of whole blood were used in serial fashion; the weight (or volume) of blood is reported as the total for the two, but the leukocyte counts before and after processing are reported for each bag separately. For pediatric size units, a single bag of PRC or whole blood was used, and the leukocyte counts before and after are reported separately for the first half of the bag contents, and for a second sample representing the second half of the bag.

Use of automatic counters for the leukocyte depleted filter effluents provides incorrect results, because automatic counters are designed to be operated in the range of normal leukocyte content of whole blood and of normal PRC. Thus, the normal operating range of automatic counters is 10 to 1000 times the levels reached in the examples herein; as a consequence, automatic counter data at these low levels are not reliable. Counts were therefore done manually using normal chamber count technique.

Bag (i.e., influent) counts were determined using a Model ZM Coulter Counter. The conventional centrifugal method was used to determine hematocrits.

For the examples of this invention, priming times were determined while applying a pressure of about 0.2 kg/cm$^2$ to the bag of blood or PRC, either by hand, or with a pressurizing cuff. A pressure of about 0.2 kg/cm$^2$ was determined by test to be the range of pressure developed with manual compression of the blood bag by three randomly selected laboratory technicians.

Priming time is defined as the time required for filling the test housing with fluid, and for the fluid to fill the inverted drip chamber ⅔ full (approx. 3 ml).

For Examples 1–168, pressure head during the tests was adjusted as required to maintain flow of 4 cc/minute for the adult (62 cm$^2$) device and 2 cc/minute for the pediatric (32 cm$^2$) device. If during a test the pressure required to maintain the required 4 or 2 cc/minute flow reached 100 cm of fluid pressure head, or about 0.1 kg/cm$^2$, it was held at that pressure until flow fell to below respectively 1 or 0.5 cc/minute, at which time the test was terminated. Thus, if the final flow for an adult filter is reported to have exceeded 1 cc/minute or 0.5 cc/minute for a pediatric size unit, all of the blood had been withdrawn from the bag, and the device was not clogged. If the flow rate during a test fell to or below the limits noted above, the device was considered to have clogged, and the residual weight in the bag is reported.

For examples 169–210, pressure head during the tests was adjusted as required to maintain flow of 6 cc/minute. If during a test the pressure required to maintain a 6 cc/minute flow rate reached 115 cm of fluid pressure head, or about 0.11 kg/cm$^2$, it was held at that pressure until flow fell to below 1 cc/minute, at which time the test was terminated. If the volume of PRC left in the bag was less than 30 cc, the filter was considered to have successfully passed that unit of PRC, as that was determined by test to be the probable outcome during bedside service.

Minimal samples of approximately 5 ml were taken from each bag of blood or PRC used for determination of influent characteristics. Where more than one unit of blood or PRC was used, they were delivered sequentially and were individually sampled and assayed.

Leukocyte (WBC) counts are reported per microliter (1 microliter equals 1 mm$^3$) of fluid. Dilutions for counting varied from 1 count = 100 WBC of relatively fresh blood to 1 count = 50 WBC for tests using blood over 10 to 14 days old.

The elements used in the examples were unless otherwise noted of disc form, 64.1 mm diameter for use in the pediatric size device, and 88.9 mm diameter at assembly for use in the adult size device. The stacked layers of elements, with a total thickness of $t_e$ were assembled into a housing as described above, with a clearance of $t_h$ between the faces of the two plenums, i.e., between the tips of the ridges 26 on the inlet plate 20 and the tips of the ridges 34 on the outlet plate 31, as shown in FIG. 1. After piercing the blood bag, the filters were primed by manual pressure applied to the bag, or with a blood pressure cuff pressurized to approximately 0.2 kg/cm$^2$, after which whole blood or packed red cells was passed by gravity and product assays made in the manner described in the preceding part of this section.

Losses of red cells due to adsorption were, unless noted, too small to be detected. For the examples 169–210 losses due to hold-up can be calculated as $=(47t_h+12)$cc.

Pore diameters of filter media were determined using the modified OSU F2 method and are reported as the diameter of hard particle at which 99.9% of the incident particles were removed. The F2 test used in making pore size measurements is a modified version of the F2 test developed in the 1970's at Oklahoma State University (OSU). In the OSU test, a suspension of an artificial contaminant in an appropriate test fluid is passed through the test filter while continuously sampling the fluid upstream and downstream of the filter under test. The samples are analyzed by automatic particle counters for their contents of five or more preselected particle diameters and the ratio of the upstream to downstream count is automatically recorded. This ratio is known in the filter industry as the beta ratio.

The beta ratio for each of the five or more diameters tested is plotted as the ordinate against particle diameter as the abscissa, usually on a graph in which the ordinate is a logarithmic scale and the abscissa is a log$^2$ scale. A smooth curve is then drawn between the points. The beta ratio for any diameter within the range tested can then be read from this curve. Efficiency at a particular particle diameter is calculated from the beta ratio by the formula:

$$\textit{Efficiency, percent} = 100(1 - 1/beta)$$

As an example, if beta=1000, efficiency=99.9%.

Unless otherwise stated, the removal ratings cited in the examples presented herein are the particle diameters at which beta=1,000, hence, the efficiency at the removal ratings cited is 99.9%.

In the modified F2 test, efficiencies in the range of from 1 to 20–25 micrometers were determined using as a test contaminant an aqueous suspension of AC fine test dust, a natural silicious dust supplied by the AC Spark Plug Company. Prior to use, a suspension of the dust in water was mixed until the dispersion was stable. Test flow rate was 44 to 100 liters per minute per square foot of filter area, a range over which the results are unaffected.

The data applicable to examples 1–168 is presented as follows:

(a) Data pertinent to the manner of preparation and to the adsorptive and filtration capabilities of the examples are presented in Table A.

(b) Behavior observed while processing blood products through the filters is presented in Tables 1 through 16.

The data of Table A are presented as follows:

Column A lists the example numbers and the table numbers in which the blood data are presented.

Column B lists the sequence of the multiple individual filtering elements used in each test assembly. The upstream gel prefilter element (number one) in examples 1–168 unless noted comprises acrylic bonded needle punched PET. The remaining elements are all made of melt blown PBT. The microaggregate removal element comprises layers 2a, 2b, 2c, 3 and 4, with 2a, 2b and 2c hot compressed together to form a subassembly, and layers 3 and 4 hot compressed separately. Layer 5 is the adsorption element, formed as a single layer by hot compression.

Column C lists fiber surface areas in units of square meters per gram. Column D lists the element apparent (bulk) densities in units of grams per cc. Column E lists element thickness, in centimeters. Column F lists the fiber surface area in units of square meters for each of the elements ($A_t = A_f \times \rho \times t \times 62$). Column G lists the fiber diameter Dp calculated from BET measurement of surface area (fiber diameter=$(0.345 A_f)^{-1}$ micrometers), except for the gel-prefilter which was estimated microscopically. Column H lists the pore size as determined by the modified OSU F2 test, in micrometers, also excepting the pore diameter of the gel-prefilter which was estimated microscopically. Column I lists the CWST values for each layer.

Examples 1–18 were made as indicated in Table A. The CWST values listed are those of media of which the surfaces had not been altered.

Examples 19 to 34, presented in Table 2, were also run using five layers. Of these, the first was identical to that of Examples 1 to 18; the microaggregate filter was identical to that of Examples 1 to 18 except that it was radiation grafted to a CWST of 59 dynes/cm. The fifth preform was identical to that of Examples 1 to 18 except that it was radiation grafted to a CWST of 65 dynes/cm.

Examples 35 to 38, presented in Table 3, made in the same way as Examples 19 to 34 except that the number 3 and 4 layers had been radiation grafted to a CWST of 75, rather than 59, were tested using whole blood with CPDA-1 additive. Average efficiency for the second unit is substantially reduced compared with the results obtained in Examples 19 to 34 (Efficiencies obtained with whole blood and with PRC may be meaningfully compared because whole blood is a diluted form of PRC.).

Examples 39 to 42, presented in Table 4, were tested using packed red cells and illustrate the effect of increasing the CWST of the elements of Examples 19 to 34. The microaggregate removal element had CWST of 81, while the adsorption element had a CWST of 75 dynes/cm. Compared with Examples 19 to 34, both capacity and efficiency are reduced.

Examples 43 and 44, presented in Table 5, further illustrate the effect of increasing the CWST of the microaggregate removal and adsorption elements of the devices of Examples 19 to 34. Examples 43 and 44 are identical to Examples 19 to 34, except that the CWST of the second layer is 81 dynes/cm, the third and fourth layers have CWST's of 77 dynes/cm, and the adsorption element has a CWST of 81 dynes/cm. The data show that efficiency for the second unit of PRC is greatly reduced.

Examples 45 to 48, presented in Table 6, were run using the configurations of Examples 19 to 34, except that the fiber surfaces of the second, third, fourth, and fifth layers had been modified to a CWST in excess of 94 dynes/cm. The data show that both efficiency and capacity are reduced from those reported in Table 2 for Examples 19 to 34.

Examples 1 to 18 of Table 1, Examples 19 to 34 of Table 2, Examples 35 to 38 of Table 3, Examples 39 to 42 of Table 4, Examples 43 to 44 of Table 5, and Examples 45 to 48 of Table 6, were all made using the same basic construction, but with the CWST ranging from 52 (unmodified) to greater than 94 dynes/cm.

The results obtained vary from less than optimal at 52 dynes/cm, to optimal at 59–65 dynes/cm, to somewhat less effective with respect to both efficiency and capacity for CWST values in the range from 65–75 to greater than 95 dynes/cm. The Example group 19 to 34 represents a preferred configuration of this invention.

Nevertheless, it should be kept in mind that all of these examples are superior to all currently available devices for bedside administration of red cells.

Examples 49 to 52, presented in Table 7, were prepared in the same manner as the pediatric size examples of group 19 to 34 except as follows: In Example 49, the gel prefilter element was omitted. In Example 50, the second layer was also omitted. In Example 51, the third layer was omitted in addition to the previous two. In Example 52, only the adsorption element was used. As may be seen in Table 7, the volume passed prior to clogging was decreased as each layer was removed, from an average of 308 ml to, respectively, 116, 46, 35, and 34 ml. The superiority of the stepped pore prefiltration system of this invention is thus clearly illustrated.

Examples 53 to 56, presented in Table 8, were part of a study to determine the preferred thickness range of the gel prefilter element, the function of which is to remove gels and very large aggregates, together with smaller aggregates which are suspended in the gels. These examples used a high loft, needle punched nonwoven made using approximately 23 micrometer fibers, which had been hot precompressed to proportionally smaller thickness and then further compressed at assembly to the thicknesses noted. The data of Table 8 may be compared with Examples 19 to 34, having been prepared in the same manner except with respect to the thickness of the prefilter element. The data shows loss of capacity at thicknesses at and below 0.56 mm.

Examples 19 to 34 have a gel prefilter element thickness of 0.90 mm. A number of tests run at 0.65 and 1.14 mm have shown very nearly equal results. Based on these data, the preferred range is in excess of about 0.6 mm.

The upper end of the range has not been explored, beyond the test at 1.14 mm. Based on post-test microscopic examination, we believe it to be probable that considerably thicker first layers up to 2 to 3 mm could be used with good results. Such relatively large thicknesses are not, however, desirable, as they would result in increased hold-up. For example, in the adult size housing used in these tests (62 cm$^2$ of effective area), the addition of 1 mm in thickness increases hold-up volume by 6.2 cc. Any increase is very undesirable.

Tests were run using the make-up of Examples 19 to 34 with the gel prefilter element made at the same density but using a starting weight of 11 mg/cm$^2$ and then compared post-test microscopically with the 8.8 mg/cm$^2$ element. The 11 mg element, which is 25% thicker, was seen to provide more space for gel collection than necessary, and based on this, the preferred weight using PET 23 micrometer fiber is 8.8 mg/cm$^2$. Lower weights may be used, but with the risk of not providing the capacity to pass two PRC units without clogging, which is an objective of this invention.

Fiber diameters other than 23 micrometers may be used for the gel prefilter, as long as the average pore diameter remains in the desired range. If fibers with average diameter differing from about 23 micrometers are used, the weight W per unit area to provide approximately equal pore diameter can be calculated with adequate accuracy for fibers of diameter d by the formula:

$$W = 8.8 \frac{d^2}{529} \text{ mg/cm}^2$$

and $20 < d < 26$

Means to accurately measure pore diameters in the range in which the gel prefilter is effective are not readily available. A satisfactory means to verify that a given material which has been compressed to a thickness of 0.9 mm has a pore diameter within the desired range of the gel prefilter in accordance with this invention employs the following procedure:

The material to be tested made to a weight of 8.8 mg/cm$^2$ is wetted by immersing it in a solution of isopropyl alcohol followed by placing the material in a holder in which the test thickness is 0.075 cm and in which air pressure can be applied while monitoring air flow. In order to function within the parameters discussed above, the pressure developed at an air flow rate of 0.5 cms/second should fall within the range of from about 3.5 to about 8.5 cm water column and preferably between about 4 and about 6.5 cm water column.

Example 57 is directed to means by which the resistance to clogging of devices in accordance with this invention may be further increased. This may be accomplished by varying the pore size of the microaggregate removal element continuously rather than stepwise.

Examples 58 to 65 were prepared as presented in Table A, and their behavior in processing PRC is presented in Table 9. The first four layers are identical with the first four of Examples 19 to 34. The adsorption element consists of five layers of 4.5 micrometer PBT fibers radiation grafted to a CWST of 59 dynes/cm and then hot precompressed to form a single preform 0.251 cm thick having a density of 0.252 g/cc, and, in the adult size, a BET fiber surface area of 1.77 square meters, and an F2 pore size rating or average pore diameter of 6.9 micrometers. Total fiber surface area of the five layers was 4.07 square meters. Total volume of the five layers was 33.3 cc.

Examples 66 to 73, also presented in Table 9, were similar to Examples 58 to 65 except that the third preformed layer was made using 4.5 micrometer fibers compressed to a thickness of 0.069 cm and a density of 0.18 g/cc, with an F2 pore diameter rating estimated to be 15 micrometers, and the fourth layer was made using 4.5 micrometer fibers precompressed to a thickness of 0.061 cm and a density of 0.21 g/cc, with an estimated F2 pore diameter rating of 12 micrometers. The adsorption element, comprising five layers of 4.5 micrometer diameter web radiation grafted to a CWST of 59 dynes/cm, was hot compressed to a single 0.277 cm thick preform of density 0.229 g/cc and an F2 pore diameter rating of 7.4 micrometers. The resulting data are shown in Table 9.

The data for Examples 58 to 65 and 66 to 73 are compared with those of 19 to 34 and 96 to 97 in Table 10. The performance with respect to leukocyte removal efficiency of Examples 19 to 34 is clearly superior to that of Examples 58 to 65, which in turn is superior to Examples 66 to 73. This is surprising, because the surface area available for removing leukocytes by adsorption in the 58 to 65 group and the 66 to 73 group is identical, i.e., both have 4.07 square meters of fiber surface area. The significant difference between these two groups of examples is that the pore diameter of the number 5 element of Examples 58 to 65 (6.9 micrometers) is smaller than that of Examples 66 to 73 (7.4 micrometers). Smaller pore diameter, therefore, is seen to improve efficiency. This conclusion is confirmed when Example group 19 to 34 is compared with Example group 58 to 65. The surface area of Example group 19 to 34 is 3.29 square meters by BET surface area measurement, i.e., it is smaller than that of Example group 66 to 73 (4.07 square meters). Yet Example group 19 to 34 has better efficiency. Again, the pore size of the downstream element of Example group 19 to 34 (6.1 micrometers) is smaller than that of Example group 66 to 73 (6.9 micrometers). The conclusion can thus be drawn that the smaller pore size of the adsorption element of the 19 to 34 group is the factor which accounts for its superior performance compared with elements of larger pore diameters.

Examples 96 and 97, shown in both Tables 10 and 15, provide further evidence of the effect of pore size of the downstream element. As noted in Tables A and 10, and the descriptive paragraph devoted to Table 15, the structure of Example 96 and 97 differ from that of Examples 58–65 only in that:

(a) The adsorption element contains less fiber, and the element assembly has a total surface area of 3.13 M$^2$.

(b) The average pore diameter of the adsorption element is 6.6 micrometers.

Despite the substantially smaller fiber surface area available for adsorption and their smaller thickness (0.145 to 0.251 cm), Examples 96 and 97 perform significantly better than Examples 58 to 65. The improvement can be due only to the smaller pore diameter of Examples 96 and 97.

Examples 103–106, shown in Table 13, were prepared in the same manner as examples 19 to 34 of Table 2, except that the adsorption element was compressed to greater density and smaller Dp (pore diameter). Four tests of each density of this group were run using PRC derived from blood drawn 2 to 4 days prior to the test. The tendency of this relatively fresh PRC to cause clogging is less than with older blood, such as was used at least in part for the tests reported elsewhere herein.

The data of Table 13 indicate that when used with fresh blood, pore sizes as small as about 4 micrometers can be used, while achieving the objective of passing two units of PRC prior to clogging. Parenthetically, all the tests in this series showed 100% removal of leukocytes.

Thus, for use with PRC derived from blood drawn about four days or less prior to its use in transfusion, a lower limit of 4 micrometers is preferred, and a lower limit of 4.2 micrometers is more preferred.

Thus, pore diameter can strongly influence leukocyte removal efficiency. This was an unexpected discovery, as it is contrary to the belief that leukocyte removal by fibrous media is a function only of surface area. As noted above, while granulocytes are larger than red cells, lymphocytes, which in normal whole blood account for 20 to 40% of all of the leukocytes, are comparable to the red cells in size.

By taking advantage of this discovery, it has been possible to reduce the blood hold-up volume by about 8% compared with Examples 58 to 65, and 16% compared with Examples 66 to 73. These are significant reductions, in effect reducing the cost of transfusing a single unit by about $3 to $6 U.S. or more based on present hospital costs and blood bank pricing.

Examples 74 to 78, presented in Table 11, were run at a flow rate of 4 cc/minute of PRC in filter housings with 32 cm$^2$ of effective flow area, in this respect equal to the pediatric size of device, but with flow rate and total quantity of fibrous medium equivalent to that contained in the adult size units of Examples 19 to 34 (a preferred configuration). This was accomplished by use of eight layers, as follows: The first and second layers were each identical with the first layer of group 19 to 34. The third layer was similar to the second layer of group 19 to 34, but used 15 mg/cm$^2$ each of 15, 10 and 7 micrometer fiber diameter medium which were laid up and hot formed to a disc 0.15 cm thick. The fourth, fifth, sixth, and seventh layers were similar to layers numbered 3 and 4 of Examples 19 to 34, except that they were compressed respectively to preforms of density 0.18, 0.20, 0.22, and 0.23 g/cc. The eighth and last layer was equal in fiber diameter and density to that of group 19 to 34 but twice the weight of fibers was compressed to a preform of twice the thickness, i.e., to 0.304 cm. The data resulting from tests of these assemblies using PRC is shown in Table 11. Capacity is seen to be adequate albeit marginally so for fresh blood, but is quite inadequate for blood aged more than a few days. Comparing these data with those of Examples 19 to 34, the advantages of using the same total quantity and type of each fibrous medium in a device with larger cross section area become apparent.

Examples 79 to 85, presented in Table 12, show data obtained when "Adsol blood" was used. Except for this group of examples, all of the whole blood and packed red cells used in the examples were run using CPDA-1 processed blood. CPDA-1 is a combination of anti-coagulants and nutrients designed to increase the period during which the red cells remain effective when transfused into a patient. In CPDA-1 whole blood or CPDA-1 PRC, the red cells are suspended in plasma; due to the higher red cell concentration in PRC (hematocrit generally in the 70 to 80% range), its viscosity is quite high, and for this reason capacity for PRC tends to be less than capacity with whole blood, for which the hematocrit is lower, and viscosity is much lower.

Within the last several years, a new class of blood product has been developed in which after centrifuging to concentrate the red cells to near to 100%, they are resuspended in a saline solution containing preservatives which extend the useful life of the red cells by about 7 days compared with the CPDA-1 system. This class of blood product has been defined as "products in which the red cells are suspended in a physiological fluid medium". The Adsol system is one such system currently seeing some use in the USA and may be considered as representative of others in the USA, Europe, and Japan.

As this type of blood product contains only a very small proportion of the original plasma and the red cells have been resuspended in the low viscosity physiological fluid, viscosities are even lower than those of whole blood. Examples 79 to 85 used the form of device employed in Examples 66 to 73, all run on the device sized for pediatric service. The data show faultless performance on Adsol blood, despite the fact that the devices of 79 to 85 and 66 to 73 are not the most preferred form of this invention.

Devices having the configurations of Examples 19 to 34, 58 to 65, 66 to 73, and others were run using whole blood with CPDA-1 anti-coagulant. Behavior with respect to capacity and efficiency were generally similar to the data reported for the Adsol product.

Examples 86 to 95 are presented in Table 14. Example 90 was not actually performed; the data entered are the averages of Examples 19 to 34. Examples 86 to 89 and 91 to 95 were performed, and are similar to example 90 except that the adsorption element densities and thicknesses were varied, while the weight was held constant. As may be seen in Table 14, the pore diameter is a critical determinant of efficiency, which for the first unit of PRC transitions from 87%, at a pore diameter of 7 micrometers, to 99.2% at 6.2 micrometers, and to 100% at 6.1 micrometers. Leukocyte removal efficiency for the second unit of PRC changes in parallel fashion, from about 70% at 6.7 to 7 micrometers, to 99.6% at 6.1 micrometers, and to 100% at 6.0 micrometers. From these data, it is seen that, for the adsorption element of a device made using 25 mg/cm$^2$ of 2.6 micrometer diameter fibers, a preferred upper limit for pore diameter is about 6.7 micrometers, while a more preferred limit is 6.3 micrometers.

Below about 6.1 micrometer pore diameter all of the examples in this group showed essentially 100% leukocyte removal efficiency for two units of PRC, and while there are some instances of clogging, satisfactory data are seen at as low as 5.5 micrometers. Hence a preferred range of pore diameter is about 5.5 to 6.7 micrometers, while a more preferred range is about 5.8 to 6.3 micrometers.

Examples 96 to 101 are presented in Table 15, and described in Table A. These examples were prepared in the same way as Examples 58 to 73, except that the downstream layer was made using three instead of five layers of 4.5 micrometer fibers hot precompressed to the thicknesses and densities noted. Total surface area of the five elements in the pediatric size used was 1.51 M$^2$, which for purposes of comparison (ref. Table 10) calculates to 3.13 M$^2$ in the adult size. As may be seen in Table 15, removal efficiencies of 100% for both the first and second units are obtained at pore diameters below about 6.6 micrometers; this may be compared in Table 10 with the onset of lower efficiency at density 0.255 g/cc and pore diameter 6.9 micrometers for Examples 58 to 65, and with the still lower efficiency at density 0.229 g/cc and pore diameter 7.4 micrometers of Examples 66 to 73. From these data, it may be seen that a preferred value for the upper limit of pore diameter is about 7.5 to 8 micrometers, and a more preferred value is 6.6 micrometers. Below 6.6 micrometers efficiencies remain at 100%, but frequency of clogging is seen to increase, in consequence of which a preferred lower limit is about 5 to 5.5 micrometers, and a more preferred limit is 6 to 6.5 micrometers.

Taken together, Examples 19 to 34, 58 to 65, 66 to 73, 86 to 95, and 96 to 101 indicate a preferred F2 pore diameter range of 5.0 to 8 micrometers, and more preferred range of 6 to 6.7 micrometers. These limits of preference are discussed in more detail below.

The Preferred Limits of Pore Diameter

As the data of examples 1–107 were reviewed, a number of conclusions were drawn in order to define the preferred range of pore diameter.

(a) Based on examples 102–106 of Table 13, tested using only fresh PRC, a low limit of 4 micrometers was preferred, with 4.2 micrometers more preferred.

(b) Based on examples 86 to 95 of Table 14, an upper limit of 6.7 micrometers was seen as preferred, with 6.3 micrometers more preferred. As a lower limit 5.5 micrometers was preferred, with 5.8 micrometers more preferred.

(c) The data presented in Table 10 suggest a range no narrower than 6.1 to 6.6 micrometers as most preferred; further, since the results for Examples 66–73 of Table 9 are far better than any product available as of this writing, a less preferred upper limit of 7.4 micrometers is justified.

(d) Finally, a review of examples 19–34, 58–65, 66–73, 86–95 and 96–100 taken together indicated a preferred range of 5 to 8 micrometers, and a more preferred range of 6 to 6.7 micrometers.

As to the low limit, since some physicians prefer to use only fresh blood for patients such as those with disabilities such as thalassemia, a preferred low end pore diameter should be 4 micrometers.

Taken together with the other considerations listed above, a preferred range is 4 to 8 micrometers. The lower part of this range is preferred for use with recently drawn PRC, while the upper part is preferred for use with older PRC.

The devices used in Examples 107 to 168 (see Table 16) were prepared in the same manner as examples 19 to 34 except that the medium used to make the gel prefilter had been scrubbed and rinsed and therefore contained no surfactant. Examples 107–119, were prepared with no surface modification, and had CWST of 52 dynes/cm. Examples 120 to 168 comprise elements which, except for the gel prefilter, were radiation-grafted (using mixtures of HEMA and MA and a minor amount of tertiary butyl alcohol to assist wetting) to modify their CWST valves over the range from 63 to 109 dynes/cm. Except for the absence of surfactant from the gel prefilter, and their varying CWST values, Examples 120 to 168 were equal in construction to examples 19 to 34.

All of the examples 107 to 168 showed 100% removal of leukocytes for the first unit of PRC passed, and the average efficiency in each group listed in Table 16 for the second unit exceeded 96%.

It is seen in Table 16 that clogging prior to passage of two units occurs with greater frequency when the CWST of the filter medium is below 75 dynes/cm. This may be related to the surface tension of the PRC, which, as noted above, has been reported to be 73 dynes/cm for the plasma and 64.5 dynes/cm for the red cells.

Based on the data of Table 16, a preferred value of the CWST of filter media is in excess of 63 dynes/cm; a more preferred value is in excess of 70 dynes/cm; and a still more preferred value is in excess of 75 dynes/cm. It should, however, be noted that the data for all of the examples are better than any product now on the market.

During the course of preparing examples 1–210, filter assemblies with CWST's of 54 dynes per cm were made and tested with satisfactory results; however, CWST values only two units different from untreated PBT fiber are considered marginal with respect to maintaining consistent performance, hence 54 dynes/cm is a less preferred value of the CWST.

The needled web used in examples 169 et seq was scrubbed prior to use to remove the fiber lubricant, rinsed with water, and then dried. The melt blown web used was unless otherwise noted radiation grafted to obtain a CWST of 64 dynes/cm.

Preform thickness was measured using a 7.7 cm diameter anvil and with an applied pressure of 4.3 g/cm$^2$.

The filter assemblies used in examples 169–186, presented in Table 17, comprised three preforms.

For preform number one, the 23 micrometer needled non-woven web described above was hot calendered to a thickness of 0.076 cm. For preform number two, a layer of 23 micrometer average fiber diameter 0.0077 g/cm$^2$ needled non-woven web was laid over a 20 micrometer average fiber diameter 0.0081 g/cm$^2$ ungrafted melt blown web, and the two hot calendered in assembly to a thickness of 0.102 cm. The above two preforms were combined in the order listed, prewetted with isopropyl alcohol, and air passed at 0.5 cms/second; pressure drop for ten such assemblies ranged from 5 to 7 cms of water column.

For preform number three, seven layers of melt blown web were used. In order, these were: one layer of 3.5 micrometer diameter fiber at 0.0069 g/cm$^2$; one layer of 3.0 micrometer diameter fiber at 0.0052/cm$^2$; one layer of 2.6 micrometer diameter fiber at 0.0063 g/cm$^2$; and four layers of 2.4 micrometer fiber diameter at 0.0061 g/cm$^2$ per layer, all seven layers calendered in assembly to a thickness of 0.296 cm, for an average density of 0.145 g/cc.

In the above construction, the first and second preforms together constitute a first element, denoted the gel prefilter element. The first three layers of the third preform constitute the microaggregate removal element, although this element also contributes to removal of leukocytes by adsorption. The last four layers of the third preform constitute the adsorption element.

In order to make it possible to determine the pore diameters of the three layers which constitute the microaggregate element, and the pore diameter of the adsorption element, each of the three microaggregate layers was underlaid prior to hot compression by a layer of an open pored ungrafted separation disc. The 0.004 cm thick separation discs had an average pore diameter greater than about 100 micrometers, hence had no significant effect on performance of the assembly, other than a thickness increase of 3×0.004=0.012 cm. Filter assemblies so prepared were used in all of the examples 169-210. By this means, the layers were readily separated in order to determine their pore diameters by OSU-F2 testing. Layers number 1, 2 and 3 of the third preform had pore diameters respectively of about 19, 16 and 13 micrometers, and the remaining group of four layers varied in pore diameter from 6.5 to 8.2 micrometers among six sample groups. The three preforms when assembled had a total thickness $t_e$ of 0.474 cm, and these were assembled into a housing with ridge to ridge clearance $t_h$ of 0.444 cm, thereby compressing the element assembly to 0.444 cm.

Examples 169-174 presented in Table 17 were performed using PRC 24 days old. All six tests successfully met the criterion noted above (i.e., less than 30 cc residual with pressure head of 115 cm of water and flow rate <1 cc/minute).

Examples 175-180 were performed with PRC of average age 34.5 days; five of the six tests met the completion criterion.

Examples 181-186, run with two day old PRC, met the completion criterion, and more important, show 100% efficiency of leukocyte removal for the first unit, and an average efficiency of 98.8% for the second unit.

Examples 1-168 describe devices for use in removing leukocytes from PRC, but these examples are directed primarily to use with relatively fresh (recently drawn) PRC, and are better suited for applications in which fresh PRC is used. Of more than 100 units of PRC listed as used in examples 1-168, only six more than 20 days old were used with filters of the type which are the subject of this invention. Of the six, two which used 29 and 30 day old PRC clogged prior to completing delivery of two units.

In U.S. hospital practice, PRC anti-coagulated with CPDA-1 is permitted to be used after storage for up to 35 days. Persons knowledgeable of U.S. hospital practice were questioned on the proportion of CPDA-1 PRC used which is more than 15-20 days of age; the mean of their estimates was 40%. The same authorities estimated that about 80% of all transfusions use two units of PRC while the remainder use only one. It is less practical for most hospitals to carry two kinds of leukocyte depletion devices, one for fresher and the other for older PRC. Thus, to be more practically useful, a device intended for use in hospital bedside service should experience at most a very small proportion of instances in which the device clogs prior to delivery of two full units of blood, even if those units are near or at the outdate limit beyond which they may not be used for transfusions. The same device must have high removal efficiency with PRC of all ages, preferably over 99.5% to 99.9% for the first unit passed, and over 95 to 99% for the second unit passed.

The test articles used for examples 1-168 are similar to the test articles of examples 169-210 in that needled non-woven of the same fiber diameter and weight is used to fabricate the gel prefilter, and the melt blown components are generally similar with respect to pore size range and CWST, but differ with respect to the mode of use of these components.

The gel prefilter of examples 1-168 uses a single layer of needled non-woven, whereas the components of the gel prefilter in accordance with examples 169-210 preferably use two layers of needled non-woven, in addition to a third layer of melt blown web. Further, the densities of the gel prefilter of examples 169-210 are substantially greater than those of examples 1-168, and the pore diameters are smaller.

In examples 187-199, shown in Table 18, the gel prefilter of examples 1-168 was tested in combination with the microaggregate prefilter and the adsorption elements of examples 169-186. By assembling the combination into a test housing with $t_h$=0.372 cm, the gel prefilter element was compressed to 0.09 cm, as in examples 1-168.

Examples 187-198 are thus identical with examples 169-186 with respect to the configuration of the microaggregate prefilter element and the adsorption element, and differ only with respect to their gel prefilters. The average age of the PRC used for testing is essentially equal for both, respectively 29.2 and 29.3 days. The gel prefilter of examples 169-186 showed only 1 of 12 clogged, for a 92% success ratio. Examples 187-198, which had been assembled with the gel prefilter of examples 1-168 showed five of twelve clogged for a 58% success ratio. The superiority of the gel prefilter of examples 169-186 for use with older PRC is, therefore, clearly demonstrated.

Compared with examples 1-168, the pore diameter of the adsorption element of examples 169-198 is larger, with a preferred pore diameter in excess of 6.5 micrometers; examples 1-168 show preferred ranges of pore diameter in excess of 4, 5 and 5.5 micrometers respectively.

The effect of using smaller pore diameter adsorption elements on the ability to successfully pass two units of older PRC is shown by examples 199-210, shown in Table 19. These were prepared in the same manner as examples 169-186, except that the preform comprising the microaggregate and adsorption elements was hot compressed to an average density of 0.192 g/cc, and the adsorption element had a pore diameter in three tests of 5.1, 5.2 and 5.2 micrometers, which is in a preferred range derived from examples 1-168 for use with fresher PRC.

The $t_h$ setting of the housings used for examples 199-210 was adjusted such that the gel prefilter element was compressed at assembly to the same thickness as in examples 169-186.

Average age of the PRC used in examples 199-210 was 29.2 days. The data show that nine of twelve clogged, for a success ratio of 25%. This compares with a ratio of 92% for examples 169-180, indicating the desirability of the larger pore diameter of examples 169-186. Consequently, a preferred pore diameter range of this invention is greater than 5.2 micrometers.

Insofar as the upper end of the range is concerned, it is believed that the pore diameter of the adsorption element could be increased to well above 10 micrometers while maintaining substantially equal efficiency; however, we have not explored the range above 8.2 micrometer diameter because of the undesirability of increasing the hold up volume for the benefit (if any) of still fewer instances of clogging with very old blood. Nevertheless, it should be understood that a device with pore opening larger than 8.2 micrometer, or larger than 10 micrometers, would fall within the scope of this invention.

Human blood, both intra- and extra-corporeal, will under some circumstances form "rouleaux", a term applied to the condition in which the 7.5 micrometer diameter by 2 to 3 micrometer thick red cells adhere to each other in a geometric configuration resembling a roll of coins. Rouleaux tend to form in the human body as a result of viral infection, for example influenza, or the common cold, and some belief exists that the inability of rouleaux to pass through the smaller capillaries of the circulatory system contributes to the muscle discomfort accompanying these infections. In the human body, capillaries less than 7.5 micrometers in diameter under normal conditions pass red cells freely, as the individual cells deform readily. If older blood tends to form rouleaux, then this phenomenon may account for the larger pore diameter required to prevent clogging by older blood of the adsorption element of this invention.

Earlier in the application, it was stated that "... it has been widely accepted that the removal of leukocytes is accomplished by adsorption, rather than by filtration."

The disclosures of this invention confirm that leukocytes are removed by adsorption, but also lead to the discovery that, particularly for relatively recently drawn PRC, they can be removed with equal or greater efficiency and with reduced blood loss due to hold-up by a combination of adsorption and filtration, provided that the pore size of the last element of the device is in the preferred diameter range and that adequate prefiltration has been provided to prevent gels, microaggregates and other components present in the PRC when it is received from the blood bank from reaching the last element.

TABLE A

| A Example Number | B Component Sequence | C $A_f$ M²/g | D P, g/cc | E t, cm | F $A_t$, M² | G Av. Fiber Dia, μm | H Dp (μm) | I CWST, Dynes/cm | J Remarks |
|---|---|---|---|---|---|---|---|---|---|
| 1–18 (Table 1) | 1 | 0.13 | 0.10 | .090 | .08 | 23 | 50[1] | 50[2] | Total surface area for the five elements in the adult size device is 3.29 square meters[3] |
| | 2a | 0.19 | | | .09 | 15 | | | |
| | 2b | 0.29 | 0.30 | .076 | .14 | 10 | 15 | 52[2] | |
| | 2c | 0.41 | | | 0.19 | 7 | | | |
| | 3 | 0.64 | 0.20 | .064 | 0.51 | 4.5 | 13 | 52[2] | |
| | 4 | 0.64 | 0.23 | .056 | 0.51 | 4.5 | 9 | 52[2] | |
| | 5 | 0.99 | 0.167 | 0.152 | 1.77 | 2.6 | 6.1 | 52[2] | |
| 19–57 (Tables 2 to 8) | | | | | | | | | See text |
| 58–65 (Table 9) | 1 | 0.13 | 0.10 | .090 | .08 | 23 | 50[1] | 50[2] | Total surface area of five elements in the adult size device is 4.07 square meters[3] |
| | 2a | 0.19 | | | .09 | 15 | | | |
| | 2b | 0.29 | .30 | .076 | .14 | 10 | 15 | 59 | |
| | 2c | 0.41 | | | 0.19 | 7 | | | |
| | 3 | 0.64 | 0.20 | .064 | 0.51 | 4.5 | 13 | 59 | |
| | 4 | 0.64 | 0.23 | .056 | 0.51 | 4.5 | 9 | 59 | |
| | 5 | 1.77 | 0.252 | .251 | 2.55 | 4.5 | 6.9 | 59 | |
| 66–73 (Table 9) | 1 | 0.13 | 0.10 | .090 | .08 | 23 | 50[1] | 50[2] | Total surface area of five elements in the adult size device is 4.07 square meters |
| | 2a | 0.19 | | | .09 | 15 | | | |
| | 2b | 0.29 | 0.30 | .076 | .14 | 10 | 15 | 59 | |
| | 2c | 0.41 | | | 0.19 | 7 | | | |
| | 3 | 0.64 | 0.18 | .069 | 0.51 | 4.5 | 15 | 59 | |
| | 4 | 0.64 | 0.21 | .061 | 0.51 | 4.5 | 12 | 59 | |
| | 5 | 1.77 | 0.229 | 0.277 | 2.55 | 4.5 | 7.4 | 59 | |
| 74–95 (Tables 11, 12 and 14) | | | | | | | | | See text |
| 96–101 (Table 15) | 1 | 0.13 | 0.10 | .090 | .08 | 23 | 50[1] | 50[2] | *      t    Dp |
| | 2a | 0.19 | | | .09 | 15 | | | 96 0.270 0.145 6.6 |
| | 2b | 0.29 | 0.30 | .076 | .14 | 10 | 15 | 59 | 97 0.270 0.145 6.6 |
| | 2c | 0.41 | | | 0.19 | 7 | | | 98 0.280 0.137 6.1 |
| | 3 | 0.64 | 0.18 | .069 | 0.51 | 4.5 | 15 | 59 | 99 0.280 0.137 6.1 |
| | 4 | 0.64 | 0.21 | .061 | 0.51 | 4.5 | 12 | 59 | 100 0.296 0.130 5.6 |
| | 5 | 0.83 | * | * | 1.53 | 4.5 | * | 59 | 106 0.299 0.130 5.6 Total surface area of 5 elements = 3.13M²[3] |
| 102–106 (Table 13) | | | | | | | | | See text |

Rev. (b)

[1]Estimated Microscopically
[2]Surfaces Not Modified
[3]For Adult Size Device

TABLE I

| | Blood Bag Data | | | | Fluid Flow Data | | | | | | Leukocytes in Effluent | |
|---|---|---|---|---|---|---|---|---|---|---|---|---|
| Example No. | Total Fluid Weight, G Start End | No. Bags Used | Age, Days | Hematocrit, % | Priming Time Sec. | Pressure Head, Inches Start End | | End Flow Rate, cc/min | Blood Hold-Up Volume, cc | Unit No. | Bag Count No. WBC per μl | No/μl | % Removal |
| 1 | 245 150 | 1 | 4 | 80 | 20 | 12.5 | 40 | .3 | | 1 | 6000 | 0 | 100 |
| | | | | | | | | | | 2 | — | — | — |
| *2 | 652 0 | 2 | 5 | 80 | 20 | 11 | 40 | 4 | | 1 | 4950 | 0 | 100 |
| | | | | | | | | | | 2 | 3000 | 170 | 94.3 |

TABLE I-continued

| Example No. | Blood Bag Data | | | | | Fluid Flow Data | | | | | Bag Count | Leukocytes in Effluent | |
|---|---|---|---|---|---|---|---|---|---|---|---|---|---|
| | Total Fluid Weight, G | | No. Bags Used | Age, Days | Hema-tocrit, % | Priming Time Sec. | Pressure Head, Inches | | End Flow Rate, cc/min | Blood Hold-Up Volume, cc | Unit No. | No. WBC per µl | No/µl | % Removal |
| | Start | End | | | | | Start | End | | | | | | |
| 3 | 297 | 0 | 1 | 3 | 74 | 19 | 8.5 | 17.5 | 2 | | 1 | 6850 | 0 | 100 |
| | | | | | | | | | | | 2 | 5500 | 100 | 99.2 |
| 4 | 243 | 0 | 1 | 4 | 75 | 21 | 12 | 22 | 2 | | 1 | 11600 | 0 | 100 |
| | | | | | | | | | | | 2 | 10500 | 50 | 99.5 |
| 5 | 344 | 0 | 1 | 26 | 80 | 25 | 16.5 | 21 | 2 | | 1 | 2050 | 0 | 100 |
| | | | | | | | | | | | 2 | 1350 | 50 | 96.7 |
| 6 | 371 | 0 | 1 | 26 | 80 | 19 | 13 | 18.5 | 2 | | 1 | 2100 | 0 | 100 |
| | | | | | | | | | | | 2 | 1650 | 0 | 100 |
| 7 | 319 | 0 | 1 | 14 | 72 | 28 | 15 | 40 | 1.8 | | 1 | 4200 | 0 | 100 |
| | | | | | | | | | | | 2 | 2350 | 75 | 96.8 |
| 8 | 320 | 144 | 1 | 14 | 80 | 18 | 18 | 40 | 0.49 | | 1 | 6350 | 0 | 100 |
| | | | | | | | | | | | 2 | 10950 | 150 | 99.6 |
| 9 | 315 | 0 | 1 | 6 | 78 | 19 | 12.5 | 34 | 2 | | 1 | 1350 | 0 | 100 |
| | | | | | | | | | | | 2 | 1450 | 0 | 100 |
| *10 | 631 | 0 | 2 | 8 | 78 | 25 | 11 | 25.5 | 4 | | 1 | 2450 | 0 | 100 |
| | | | | | | | | | | | 2 | 1800 | 0 | 100 |
| 11 | 296 | 107 | 1 | 5 | 85 | 18 | 13.5 | 40 | 0.47 | | 1 | 3150 | 0 | 100 |
| | | | | | | | | | | | 2 | 2050 | 0 | 100 |
| 12 | 337 | 0 | 1 | 6 | 76 | 16 | 10 | 40 | 2 | | 1 | 6550 | 0 | 100 |
| | | | | | | | | | | | 2 | 5600 | 200 | 96.4 |
| 13 | 308 | 0 | 1 | 15 | 79 | 17 | 10.5 | 34 | 2 | | 1 | 3350 | 0 | 100 |
| | | | | | | | | | | | 2 | 3000 | 75 | 97.5 |
| *14 | 658 | 0 | 2 | 17 | 80 | 69 | 21 | 40 | 3.6 | | 1 | 1900 | 0 | 100 |
| | | | | | | | | | | | 2 | 3850 | 25 | 99.4 |
| 15 | 280 | 0 | 1 | 10 | 76 | 17 | 10.5 | 29.5 | 2 | 19.4 | 1 | 2150 | 0 | 100 |
| | | | | | | | | | | | 2 | 1850 | 0 | 100 |
| 16 | 302 | 87 | 1 | 14 | 76 | 14 | 13 | 40 | 0.47 | 19.4 | 1 | 2750 | 0 | 100 |
| | | | | | | | | | | | 2 | 2600 | 25 | 99 |
| 17 | 343 | 0 | 1 | 14 | 76 | 13 | 11.5 | 40 | 2 | 19.4 | 1 | 3100 | 0 | 100 |
| | | | | | | | | | | | 2 | 2750 | 25 | 99.1 |
| *18 | 577 | 254 | 2 | 14 | 85 | 20 | 14 | 40 | 0.95 | 34.2 | 1 | 2900 | 0 | 100 |
| | | | | | 85 | | | | | | 2 | 4500 | 50 | 98.9 |

*Adult size device. All others are pediatric size.

TABLE 2

| Example No. | Blood Bag Data | | | | | Fluid Flow Data | | | | | Bag Count | Leukocytes in Effluent | |
|---|---|---|---|---|---|---|---|---|---|---|---|---|---|
| | Total Fluid Weight, G | | No. Bags Used | Age, Days | Hema-tocrit, % | Priming Time Sec. | Pressure Head, Inches | | End Flow Rate, cc/min | Blood Hold-Up Volume, cc | Unit No. | No. WBC per µl | No/µl | % Removal |
| | Start | End | | | | | Start | End | | | | | | |
| *19 | 575 | 0 | 2 | 19 | 75 | 16 | 13.5 | 40 | 4 | | 1 | 1600 | 0 | 100 |
| | | | | | | | | | | | 2 | 1350 | 0 | 100 |
| 20 | 219 | 0 | 1 | 27 | 82 | 33 | 22.5 | 38 | 2 | | 1 | 1250 | 0 | 100 |
| | | | | | | | | | | | 2 | 1400 | 0 | 100 |
| 21 | 271 | 0 | 1 | 27 | 75 | 24 | 20 | 40 | 2 | | 1 | 1550 | 0 | 100 |
| | | | | | | | | | | | 2 | 2000 | 0 | 100 |
| 22 | 275 | 0 | 1 | 19 | 65 | 12 | 9 | 29 | 2 | | 1 | 2400 | 0 | 100 |
| | | | | | | | | | | | 2 | 2500 | 0 | 100 |
| 23 | 288 | 0 | 1 | 2 | 71 | 12 | 3.5 | 17 | 2 | 20.7 | 1 | 7750 | 0 | 100 |
| | | | | | | | | | | | 2 | 8150 | 150 | 98 |
| 24 | 273 | 0 | 1 | 2 | 75 | 12 | 7 | 40 | 1.9 | 20.8 | 1 | 5500 | 0 | 100 |
| | | | | | | | | | | | 2 | 4650 | 0 | 100 |
| 25 | 209 | 0 | 1 | 2 | 75 | 10 | 7.5 | 12 | 2 | 21.0 | 1 | 7950 | 0 | 100 |
| | | | | | | | | | | | 2 | 10150 | 0 | 100 |
| *26 | 561 | 0 | 2 | 17 | 79 | 33 | 23.5 | 40 | 3 | 36.1 | 1 | 2400 | 0 | 100 |
| | | | | | | | | | | | 2 | 1850 | 0 | 100 |
| 27 | 320 | 0 | 1 | 15 | 75 | 12 | 14.5 | 28 | 2 | | 1 | 500 | 0 | 100 |
| | | | | | | | | | | | 2 | 700 | 0 | 100 |
| 28 | 360 | 0 | 1 | 15 | 75 | 10 | 12.5 | 40 | 1.7 | | 1 | 3500 | 0 | 100 |
| | | | | | | | | | | | 2 | 3400 | 0 | 100 |
| 29 | 295 | 0 | 1 | 19 | 80 | 33 | 10 | 31 | 2 | | 1 | 2000 | 0 | 100 |
| | | | | | | | | | | | 2 | 2200 | 0 | 100 |
| 30 | 268 | 0 | 1 | 19 | 79 | 16 | 10 | 31 | 2 | | 1 | 1900 | 0 | 100 |
| | | | | | | | | | | | 2 | 2800 | 0 | 100 |
| 31 | 254 | 0 | 1 | 20 | 83 | 16 | 10 | 17.5 | 2 | | 1 | 950 | 0 | 100 |
| | | | | | | | | | | | 2 | 1600 | 0 | 100 |
| *32 | 526 | 0 | 2 | 18 | 81 | 18 | 14 | 40 | 3.7 | | 1 | 3200 | 0 | 100 |
| | | | | | | | | | | | 2 | 1450 | 0 | 100 |
| *33 | 729 | 0 | 2 | 9 | 67 | 12 | 11.5 | 23.5 | 4 | 36.1 | 1 | 1900 | 0 | 100 |
| | | | | | 71 | | | | | | 2 | 2250 | 20 | 99.1 |
| *34 | 620 | 0 | 2 | 10 | 75 | 15 | 11.5 | 40 | 4 | 36.1 | 1 | 2100 | 0 | 100 |
| | | | | | 78 | | | | | | 2 | 3150 | 20 | 99.4 |

*Adult size device. All others are pediatric size.

TABLE 3

| Example No. | *Blood Bag Data Total Fluid Weight, G Start | *Blood Bag Data Total Fluid Weight, G End | *Blood Bag Data No. Bags Used | *Blood Bag Data Age, Days | *Blood Bag Data Hema-tocrit, % | Fluid Flow Data Primimg Time Sec. | Fluid Flow Data Pressure Head, Inches Start | Fluid Flow Data Pressure Head, Inches End | Fluid Flow Data End Flow Rate, cc/min | Blood Hold-Up Volume, cc | Unit No. | Bag Count No. WBC per μl | Leukocytes in Effluent No/μl | Leukocytes in Effluent % Removal |
|---|---|---|---|---|---|---|---|---|---|---|---|---|---|---|
| 35 | 560 | 142 | 1 | 3 | 45 | <6 | 5.5 | 40 | .46 | 21 | 1 | 3050 | 0 | 100 |
|    |     |     |   |   |    |    |     |    |     |    | 2 | 3500 | 300 | 91.4 |
| 36 | 462 | 57  | 1 | 3 | 44 | <6 | 6.5 | 40 | .49 | 21 | 1 | 2900 | 0 | 100 |
|    |     |     |   |   |    |    |     |    |     |    | 2 | 2900 | 300 | 89.7 |
| 37 | 519 | 0   | 1 | 15 | 47 | <6 | 8.0 | 24.5 | 2 | 21 | 1 | 600 | 0 | 100 |
|    |     |     |   |   |    |    |     |    |     |    | 2 | 500 | 0 | 100 |
| 38 | 557 | 0   | 1 | 15 | 50 | <6 | 4.5 | 16.5 | 2 | 21 | 1 | 1750 | 0 | 100 |
|    |     |     |   |   |    |    |     |    |     |    | 2 | 1700 | 0 | 100 |

*Whole Blood

TABLE 4

| Example No. | *Blood Bag Data Total Fluid Weight, G Start | *Blood Bag Data Total Fluid Weight, G End | *Blood Bag Data No. Bags Used | *Blood Bag Data Age, Days | *Blood Bag Data Hema-tocrit, % | Fluid Flow Data Primimg Time Sec. | Fluid Flow Data Pressure Head, Inches Start | Fluid Flow Data Pressure Head, Inches End | Fluid Flow Data End Flow Rate, cc/min | Blood Hold-Up Volume, cc | Unit No. | Bag Count No. WBC per μl | Leukocytes in Effluent No/μl | Leukocytes in Effluent % Removal |
|---|---|---|---|---|---|---|---|---|---|---|---|---|---|---|
| 39 | 249 | 0 | 1 | 2 | 76 | 21 | 12.5 | 32.5 | 2 | 20.4 | 1 | 6200 | 0 | 100 |
|    |     |   |   |   |    |    |      |      |   |      | 2 | 5350 | 0 | 100 |
| 40 | 271 | 78 | 1 | 2 | 80 | 20 | 11.5 | 40 | .45 | 21.3 | 1 | 7200 | 0 | 100 |
|    |     |    |   |   |    |    |      |    |     |      | 2 | 7000 | 0 | 100 |
| 41 | 317 | 27 | 1 | 9 | 71 | 17 | 10.5 | 40 | .46 | 22.2 | 1 | 3950 | 0 | 100 |
|    |     |    |   |   |    |    |      |    |     |      | 2 | 3500 | 0 | 100 |
| *42 | 604 | 95 | 2 | 9 | 73 | 27 | 17.5 | 40 | .97 | 36.1 | 1 | 4650 | 0 | 100 |
|    |     |    |   |   | 75 |    |      |    |     |      | 2 | 5000 | 150 | 97 |

*Adult size device. All others are pediatric size.

TABLE 5

| Example No. | Blood Bag Data Total Fluid Weight, G Start | Blood Bag Data Total Fluid Weight, G End | Blood Bag Data No. Bags Used | Blood Bag Data Age, Days | Blood Bag Data Hema-tocrit, % | Fluid Flow Data Primimg Time Sec. | Fluid Flow Data Pressure Head, Inches Start | Fluid Flow Data Pressure Head, Inches End | Fluid Flow Data End Flow Rate, cc/min | Blood Hold-Up Volume, cc | Unit No. | Bag Count No. WBC per μl | Leukocytes in Effluent No/μl | Leukocytes in Effluent % Removal |
|---|---|---|---|---|---|---|---|---|---|---|---|---|---|---|
| 43 | 308 | 0 | 1 | 2 | 66 | 10 | 7.5 | 15.5 | 2 | 21 | 1 | 7300 | 0 | 100 |
|    |     |   |   |   |    |    |     |      |   |    | 2 | 7100 | 350 | 95.1 |
| *44 | 640 | 0 | 2 | 2 | 70 | 13 | 11 | 26 | 4 | 36 | 1 | 3900 | 0 | 100 |
|    |     |   |   |   |    |    |    |    |   |    | 2 | 5650 | 530 | 91.6 |

*Adult size device. All others are pediatric size.

TABLE 6

| Example No. | Blood Bag Data Total Fluid Weight, G Start | Blood Bag Data Total Fluid Weight, G End | Blood Bag Data No. Bags Used | Blood Bag Data Age, Days | Blood Bag Data Hema-tocrit, % | Fluid Flow Data Primimg Time Sec. | Fluid Flow Data Pressure Head, Inches Start | Fluid Flow Data Pressure Head, Inches End | Fluid Flow Data End Flow Rate, cc/min | Blood Hold-Up Volume, cc | Unit No. | Bag Count No. WBC per μl | Leukocytes in Effluent No/μl | Leukocytes in Effluent % Removal |
|---|---|---|---|---|---|---|---|---|---|---|---|---|---|---|
| *45 | 526 | 0 | 2 | 4 | 77 | 36 | 13 | 26 | 4 | 36.1 | 1 | 5550 | 0 | 100 |
|     |     |   |   |   | 76 |    |    |    |   |      | 2 | 2900 | 20 | 99.3 |
| 46 | 273 | 0 | 1 | 11 | 76 | 23 | 13.5 | 40 | 1.7 | 20.4 | 1 | 6150 | 50 | 99.2 |
|    |     |   |   |    |    |    |      |    |     |      | 2 | 7800 | 650 | 91.7 |
| 47 | 271 | 76 | 1 | 15 | 86 | 26 | 31.5 | 40 | 0.49 | 20.4 | 1 | 5300 | 0 | 100 |
|    |     |    |   |    |    |    |      |    |      |      | 2 | 6250 | 0 | 100 |
| 48 | 286 | 0 | 1 | 27 | 75 | 26 | 14 | 40 | 2.0 | 19.4 | 1 | 1200 | 0 | 100 |
|    |     |   |   |    |    |    |    |    |     |      | 2 | 1000 | 0 | 100 |

*Adult size device. All others are pediatric size.

TABLE 7

| Example No. | Blood Bag Data Total Fluid Weight, G Start | Blood Bag Data Total Fluid Weight, G End | Blood Bag Data No. Bags Used | Blood Bag Data Age, Days | Blood Bag Data Hema-tocrit, % | Fluid Flow Data Primimg Time Sec. | Fluid Flow Data Pressure Head, Inches Start | Fluid Flow Data Pressure Head, Inches End | Fluid Flow Data End Flow Rate, cc/min | Blood Hold-Up Volume, cc | Unit No. | Bag Count No. WBC per μl | Leukocytes in Effluent No/μl | Leukocytes in Effluent % Removal |
|---|---|---|---|---|---|---|---|---|---|---|---|---|---|---|
| 49 | 313 | 173 | 1 | 14 | 78 | 12 | 15.5 | 40 | .43 | 18 | 1 | 2500 | 0 | 100 |
|    |     | 116** |   |    |    |    |      |    |     |    |   |      |   |     |
| 50 | 338 | 249 | 1 | 14 | 78 | 17 | 40 | 40 | .44 | 16 | 1 | 3000 | 0 | 100 |
|    |     | 46** |   |    |    |    |    |    |     |    |   |      |   |     |
| 51 | 252 | 195 | 1 | 14 | 80 | 17 | 40 | 40 | .47 | 14 | 1 | 2300 | 0 | 100 |
|    |     | 35** |   |    |    |    |    |    |     |    |   |      |   |     |
| 52 | 290 | 231 | 1 | 14 | 76 | 13 | 40 | 40 | .44 | 11 | 1 | 2500 | 0 | 100 |

TABLE 7-continued

| Example No. | Blood Bag Data | | | | | Fluid Flow Data | | | | | Leukocytes in Effluent | |
|---|---|---|---|---|---|---|---|---|---|---|---|---|
| | Total Fluid Weight, G | | No. Bags Used | Age, Days | Hema-tocrit, % | Priming Time Sec. | Pressure Head, Inches | | End Flow Rate, cc/min | Blood Hold-Up Volume, cc | Unit No. | Bag Count No. WBC per μl | No/μl | % Removal |
| | Start | End | | | | | Start | End | | | | | | |
| | | 34** | | | | | | | | | | | | |

**Volume collected downstream of the filter.

TABLE 8

| Example No. | Blood Bag Data | | | | | Fluid Flow Data | | | | | Bag Count No. WBC per μl | Leukocytes in Effluent | | Thickness Layer 1, mm |
|---|---|---|---|---|---|---|---|---|---|---|---|---|---|---|
| | Total Fluid Weight, G Start | End | No. Bags Used | Age, Days | Hema-tocrit, % | Priming Time Sec. | Pressure Head, Inches Start | End | End Flow Rate, cc/min | Blood Hold-Up Volume, cc | Unit No. | | No/μl | % Removal | |
| 53 | 294 | 67 | 1 | 15 | 83 | 22 | 12.5 | 40 | 0.49 | 18.5 | 1 | 2700 | 0 | 100 | 0.56 |
| | | | | | | | | | | | 2 | 2850 | 0 | 100 | |
| 54 | 346 | 0 | 1 | 15 | 69 | 15 | 11 | 40 | 2 | 19.9 | 1 | 3100 | 0 | 100 | 0.48 |
| | | | | | | | | | | | 2 | 3900 | 0 | 100 | |
| 55 | 278 | 0 | 1 | 15 | 82 | 23 | 18.5 | 40 | 1.8 | 19.4 | 1 | 5800 | 25 | 99.6 | 0.41 |
| | | | | | | | | | | | 2 | 4200 | 450 | 89.3 | |
| *56 | 592 | 234 | 2 | 15 | 78 | 27 | 23 | 40 | 0.98 | 32.4 | 1 | 4650 | 0 | 100 | 0.36 |
| | | | | | 80 | | | | | | 2 | 2050 | 0 | 100 | |

*Adult size device. All others are pediatric size.

TABLE 9

| Example No. | Blood Bag Data | | | | | Fluid Flow Data | | | | | Bag Count No. WBC per μl | Leukocytes in Effluent | |
|---|---|---|---|---|---|---|---|---|---|---|---|---|---|
| | Total Fluid Weight, G Start | End | No. Bags Used | Age, Days | Hema-tocrit % | Priming Time Sec. | Pressure Head, Inches Start | End | End Flow Rate, cc/min | Blood Hold-Up Volume, cc | Unit No. | | No/μl | % Removal |
| 58 | 328 | 0 | 1 | 19 | 73 | 11 | 8.5 | 5.5 | 2 | 20.6 | 1 | 5450 | 0 | 100 |
| | | | | | | | | | | | 2 | 4600 | 25 | 99.5 |
| *59 | 528 | 0 | 2 | 14 | 72 | 20 | 14.5 | 39 | 4 | 38.6 | 1 | 1600 | 0 | 100 |
| | | | | 14 | 76 | | | | | | 2 | 1750 | 50 | 97.1 |
| *60 | 511 | 0 | 2 | 19 | 76 | 20 | 23.5 | 23.5 | 4 | 39 | 1 | 750 | 0 | 100 |
| | | | | 19 | 76 | | | | | | 2 | 2150 | 0 | 100 |
| 61 | 309 | 0 | 1 | 19 | 72 | 13 | 9 | 17 | 2 | 22.4 | 1 | 2150 | 0 | 100 |
| | | | | | | | | | | | 2 | 2500 | 50 | 98 |
| 62 | 350 | 0 | 1 | 17 | 70 | 14 | 14 | 21 | 2 | 23.4 | 1 | 1800 | 0 | 100 |
| | | | | | | | | | | | 2 | 1500 | 0 | 100 |
| *63 | 671 | 0 | 2 | 20 | 80 | 15 | 14.5 | 27.5 | 4 | 40 | 1 | 850 | 0 | 100 |
| | | | | 21 | 80 | | | | | | 2 | 2200 | 25 | 98.9 |
| 64 | 371 | 0 | 1 | 16 | 70 | 11 | 14 | 24.5 | 2 | 22.2 | 1 | 1800 | 0 | 100 |
| | | | | | | | | | | | 2 | 2200 | 0 | 100 |
| 65 | 294 | 0 | 1 | 16 | 70 | 15 | 12 | 16 | 2 | 23 | 1 | 1300 | 0 | 100 |
| | | | | | | | | | | | 2 | 1500 | 0 | 100 |
| 66 | 280 | 0 | 1 | 18 | 79 | 14 | 11 | 20 | 2 | 24 | 1 | 3850 | 0 | 100 |
| | | | | | | | | | | | 2 | 4050 | 750 | 81.5 |
| 67 | 310 | 0 | 1 | 18 | 79 | 9 | 11 | 13 | 2 | 24.5 | 1 | 2750 | 0 | 100 |
| | | | | | | | | | | | 2 | 2000 | 0 | 100 |
| 68 | 339 | 0 | 1 | 17 | 75 | 14 | 11 | 40 | 1.9 | 23.3 | 1 | 3000 | 0 | 100 |
| | | | | | | | | | | | 2 | 3000 | 350 | 88.3 |
| 69 | 362 | 0 | 1 | 17 | 73 | 12 | 8.5 | 11 | 2 | 24.8 | 1 | 2100 | 0 | 100 |
| | | | | | | | | | | | 2 | 2200 | 300 | 86.4 |
| 70 | 346 | 0 | 1 | 17 | 75 | 11 | 9.5 | 40 | 1.9 | 24.5 | 1 | 2850 | 0 | 100 |
| | | | | | | | | | | | 2 | 2250 | 0 | 100 |
| 71 | 347 | 0 | 1 | 16 | 73 | 19 | 16.5 | 40 | 1.8 | 23 | 1 | 2700 | 0 | 100 |
| | | | | | | | | | | | 2 | 1800 | 100 | 94.4 |
| 72 | 354 | 0 | 1 | 16 | 75 | 13 | 9 | 26 | 2 | 24.4 | 1 | 2300 | 0 | 100 |
| | | | | | | | | | | | 2 | 1300 | 0 | 100 |
| 73 | 322 | 80 | 1 | 16 | 75 | 32 | 24.5 | 40 | .47 | 25.1 | 1 | 1700 | 0 | 100 |
| | | | | | | | | | | | 2 | 1800 | 0 | 100 |

*Adult size device. All others are pediatric size.

TABLE 10

| | | Example Numbers | | | |
|---|---|---|---|---|---|
| | | 19–34 | 96–97 | 58–65 | 66–73 |
| DOWN-STREAM ELEMENT DATA | Fiber Diameter micrometers, | 2.6 | 4.5 | 4.5 | 4.5 |
| | Thickness, cm | 0.152 | 0.145 | 0.251 | 0.277 |
| | Density, g/cc | 0.167 | 0.270 | 0.252 | 0.229 |
| | Pore Diameter micrometers | 6.1 | 6.6 | 6.9 | 7.4 |
| | Surface Area, Square Meters | 3.29 | 3.13 | 4.07 | 4.07 |
| | No. of tests failing to pass two units | 0 | 0 | 0 | 1 |
| | Average efficiency for first unit, % | 100 | 100 | 100 | 100 |
| | Average efficiency for second unit, % | 99.9 | 100 | 99.2 | 95.1 |

TABLE 10-continued

| | Example Numbers | | | |
|---|---|---|---|---|
| | 19–34 | 96–97 | 58–65 | 66–73 |
| Average hold up volume of pediatric device, ml | 20.8 | 20.4 | 22.3 | 24.2 |
| Average hold up volume of the adult size device, cc | 36.1 | 35.7* | 39.2 | 43.3* |
| Volume of the fibrous elements, cc | 27.1 | 26.6 | 33.3 | 35.5 |

*Estimated datum

TABLE 13

| Example No. | Density, g/cc | Thickness, cms | % of Tests Clogged | F2 Pore dia, μm |
|---|---|---|---|---|
| 102* | 0.17 | 0.152 | 0 | 6.1 |
| 103 | 0.19 | 0.137 | 0 | 4.7 |
| 104 | 0.21 | 0.124 | 0 | 4.2 |
| 105 | 0.23 | 0.112 | 25 | 3.8 |
| 106 | 0.25 | 0.102 | 50 | 3.6 |

*Average of the data of examples 19–34.

TABLE 11

| Example No. | Blood Bag Data | | | | Fluid Flow Data | | | | | Bag Count | Leukocytes in Effluent | |
|---|---|---|---|---|---|---|---|---|---|---|---|---|
| | Total Fluid Weight, G Start End | No. Bags Used | Age, days | Hema-tocrit, % | Priming Time Sec. | Pressure Haed, Inches Start End | | End Flow Rate, cc/min | Blood Hold-Up Volume, cc | Unit No. | No. WBC per μl | No/μl | % Removal |
| 74 | 626  0 | 2 | 4 | 71 / 74 | 21 | 19.5 | 40 | 3.8 | 31.5 | 1 / 2 | 4700 / 16150 | 0 / 40 | 100 / 99.7 |
| 75 | 614  171 | 2 | 9 | 74 / 68 | 42 | 19 | 40 | 0.97 | 31.5 | 1 / 2 | 3100 / 2950 | 0 / 0 | 100 / 100 |
| 76 | 567  116 | 2 | 15 | 76 / 75 | 34 | 11 | 40 | 0.98 | 31.5 | 1 / 2 | 4500 / 6350 | 0 / 25 | 100 / 99.6 |
| 77 | 572  188 | 2 | 18 | 78 / 76 | 45 | 29.5 | 40 | 0.98 | 31.5 | 1 / 2 | 1800 / 1300 | 0 / 0 | 100 / 100 |
| 78 | 304  3 | 1 | 34 | 80 | 92 | 40 | 40 | 0.96 | 31.5 | 1 | 1900 | 0 | 100 |

TABLE 12

| Example No. | Blood Bag Data | | | | Fluid Flow Data | | | | | Bag Count | Leukocytes in Effluent | |
|---|---|---|---|---|---|---|---|---|---|---|---|---|
| | Total Fluid Weight, G Start End | No. Bags Used | Age, Days | Hema-tocrit, % | Priming Time Sec. | Pressure Head, Inches Start End | | End Flow Rate, cc/min | Blood Hold-Up Volume, cc | Unit No. | No. WBC per μl | No/μl | % Removal |
| 79 | 353  0 | 1 | 18 | 62 | 7 | 5.5 | 13 | 2 | 21.6 | 1 / 2 | 700 / 800 | 0 / 0 | 100 / 100 |
| 80 | 311  0 | 1 | 18 | 57 | 6 | 8 | 12.5 | 2 | 22.3 | 1 / 2 | 1800 / 1750 | 0 / 0 | 100 / 100 |
| 81 | 374  0 | 1 | 19 | 58 | 7 | 5 | 15.5 | 2 | 22.7 | 1 / 2 | 1350 / 1500 | 0 / 0 | 100 / 100 |
| 82 | 383  0 | 1 | 19 | 60 | 6 | 7.5 | 13.5 | 2 | 22.2 | 1 / 2 | 750 / 950 | 0 / 0 | 100 / 100 |
| 83 | 339  0 | 1 | 25 | 61 | 8 | 10 | 12 | 2 | 22.4 | 1 / 2 | 1500 / 1100 | 0 / 0 | 100 / 100 |
| 84 | 339  0 | 1 | 25 | 56 | 8 | 9 | 17.5 | 2 | 22.4 | 1 / 2 | 2300 / 2000 | 0 / 0 | 100 / 100 |
| 85 | 438  0 | 1 | 25 | 56 | 5 | 7.5 | 40 | .86 | 21.5 | 1 / 2 | 1250 / 1150 | 0 / 0 | 100 / 100 |

TABLE 14

| Example No. | Blood Bag Data | | | | Fluid Flow Data | | | | | Bag Count No. WBC per μl | Leukocytes in Effluent | | Density g/cc | Thickness, mm | Pore Dia. μm |
|---|---|---|---|---|---|---|---|---|---|---|---|---|---|---|---|
| | Total Fluid Weight, G Start End | No. Bags Used | Age, Days | Hematocrit, % | Priming Time Sec. | Pressure Head, Inches Start End | | End Flow Rate, cc/min | Blood Hold-Up Volume, cc | Unit No. | | No/μl | % Removal | | | |
| 86 | 293  26 | 1 | 3 | 77 | 13 | 10 | 40 | 0.48 | 24.9 | 1 / 2 | 6500 / 4500 | 850 / 2550 | 87 / 43.3 | 0.117 | 2.24 | 7 |
| 87 | 267  0 | 1 | 3 | 79 | 14 | 8 | 13 | 2 | 23.1 | 1 / 2 | 5300 / 4200 | 300 / 1000 | 94.5 / 74.2 | 0.128 | 2.03 | 6.7 |
| 88 | 315  ·0 | 1 | 3 | 78 | 12 | 7 | 10 | 2 | 21.9 | 1 / 2 | 7200 / 5500 | 450 / 1850 | 93.7 / 66.4 | 0.142 | 1.85 | 6.5 |
| 89 | 273  21 | 1 | 3 | 76 | 13 | 10.5 | 40 | 0.47 | 20.6 | 1 / 2 | 11050 / 9350 | 200 / 2600 | 99.2 / 72.2 | 0.157 | 1.68 | 6.3 |
| 90 | 287  0 | 1–2 | 15 | 76 | 18 | 12.5 | 32 | 1.7–4 | 20.8–36.1 | 1 / 2 | 2900 / 3100 | 0 / 12 | 100 / 99.6 | 0.167 | .152 | 6.1 |
| 91 | 317  164 | 1 | 15 | 75 | 25 | 40 | 40 | 0.48 | 20.4 | 1 / 2 | 3550 / 3450 | 0 / 0 | 100 / 100 | 0.173 | 1.45 | 6.0 |
| 92 | 337  0 | 1 | 19 | 79 | 22 | 16 | 31.5 | 0.84 | 20.4 | 1 / 2 | 2600 / 2600 | 0 / 0 | 100 / 100 | 0.180 | 1.45 | 5.9 |
| 93 | 292  147 | 1 | 21 | 84 | 36 | 39 | 40 | 0.49 | 20.4 | 1 | 1400 | 0 | 100 | 0.180 | 1.45 | 5.9 |
| 94 | 281  36 | 1 | 15 | 75 | 14 | 14 | 40 | 0.49 | 20.4 | 1 / 2 | 4900 / 5450 | 0 / 0 | 100 / 100 | 0.183 | 1.37 | 5.9 |
| 95 | 283  0 | 1 | 15 | 76 | 27 | 18.5 | 40 | 1.5 | 20.4 | 1 / 2 | 2700 / 3150 | 0 / 0 | 100 / 100 | 0.196 | 1.30 | 5.7 |

TABLE 15

| Example No. | Blood Bag Data | | | | | Fluid Flow Data | | | | Unit No. | Bag Count No. WBC per μl | Leukocytes in Effluent | | Density g/cc | Thickness, cm | Pore Dia. μm |
|---|---|---|---|---|---|---|---|---|---|---|---|---|---|---|---|---|
| | Total Fluid Weight, G | | No. Bags Used | Age, Days | Hematocrit, % | Priming Time Sec. | Pressure Head, Inches | | End Flow Rate, cc/min | Blood Hold-Up Volume, cc | | No/μl | % Removal | | | |
| | Start | End | | | | | Start | End | | | | | | | | | |
| 96 | 239 | 0 | 1 | 22 | 82 | 17 | 16 | 40 | 1.6 | 20.4 | 1 | 1700 | 0 | 100 | 0.270 | 0.145 | 6.6 |
| | | | | | | | | | | | 2 | 1600 | 0 | 100 | | | |
| 97 | 343 | 0 | 1 | 16 | 70 | 7 | 6 | 27.5 | 2 | 20.5 | 1 | 1550 | 0 | 100 | 0.270 | 0.145 | 6.6 |
| | | | | | | | | | | | 2 | 1000 | 0 | 100 | | | |
| 98 | 240 | 0 | 1 | 16 | 79 | 12 | 13 | 32.5 | 2 | 20.6 | 1 | 950 | 0 | 100 | 0.280 | 0.137 | 6.1 |
| | | | | | | | | | | | 2 | 950 | 0 | 100 | | | |
| 99 | 286 | 62 | 1 | 22 | 86 | 24 | 15 | 40 | 0.49 | 19.1 | 1 | 1600 | 0 | 100 | 0.280 | 0.137 | 6.1 |
| | | | | | | | | | | | 2 | 1600 | 0 | 100 | | | |
| 100 | 335 | 0 | 1 | 16 | 74 | 12 | 7.5 | 19 | 2 | 20.6 | 1 | 1850 | 0 | 100 | 0.296 | 0.130 | 5.6 |
| | | | | | | | | | | | 2 | 1800 | 0 | 100 | | | |
| 101 | 343 | 0 | 1 | 16 | 75 | 8 | 8 | 16 | 2 | 20.4 | 1 | 1300 | 0 | 100 | 0.299 | 0.130 | 5.6 |
| | | | | | | | | | | | 2 | 1150 | 0 | 100 | | | |

TABLE 16

| 1 Example Numbers | 2 CWST dynes/cm | 3 | 4 | 5 |
|---|---|---|---|---|
| | | Number of units passed prior to clogging | | |
| | | 0 | 1 | 2 (no clogging) |
| 107–119 | 52 | 1 | 3 | 9 |
| 119–125 | 63 | 0 | 3 | 12 |
| 126–140 | 75 | 1 | 0 | 14 |
| 141–156 | 87 | 0 | 0 | 16 |
| 157–168 | 109 | 0 | 1 | 11 |

TABLE 17

| Example No. | PRC DATA | | | | | | Priming Time, Seconds | LEUKOCYTE COUNT | | | | LEUKOCYTE EFFICIENCY, % | |
|---|---|---|---|---|---|---|---|---|---|---|---|---|---|
| | Volume of Two Bags, cc | Volume Remaining cc | Hematocrit, % | | Age, Days | | | Bag | | Filtrate | | | |
| | | | #1 | #2 | #1 | #2 | | 1 | 2 | 1 | 2 | 1 | 2 |
| 169 | 530 | 0 | 73 | 80 | 24 | 24 | 20 | 50 | 50 | 0 | 0 | * | * |
| 170 | 519 | 22 | 76 | 75 | 24 | 24 | 19 | 0 | 0 | 0 | 25 | * | * |
| 171 | 655 | 20 | 78 | 70 | 24 | 24 | 17 | 50 | 50 | 0 | 0 | * | * |
| 172 | 575 | 0 | 75 | 64 | 24 | 24 | 20 | 0 | 100 | 0 | 0 | * | * |
| 173 | 599 | 0 | 73 | 75 | 24 | 24 | 15 | 50 | 150 | 0 | 0 | * | * |
| 174 | 618 | 0 | 70 | 59 | 24 | 24 | 14 | 0 | 100 | 0 | 0 | * | * |
| 175 | 612 | 0 | 62 | 71 | 35 | 34 | 15 | 50 | 250 | 0 | 0 | * | 100 |
| 176 | 594 | 0 | 76 | 76 | 35 | 33 | 21 | 300 | 100 | 0 | 0 | 100 | * |
| 177 | 582 | 0 | 60 | 65 | 35 | 34 | 19 | 150 | 50 | 0 | 0 | * | * |
| 178 | 555 | 0 | 63 | 70 | 35 | 33 | 23 | 0 | 150 | 0 | 0 | * | * |
| 179 | 475 | 0 | 70 | 74 | 35 | 35 | 20 | 300 | 50 | 0 | 0 | 100 | * |
| 180 | 500 | 100 | 76 | 71 | 35 | 35 | 20 | 100 | 150 | 0 | 0 | * | * |
| 181 | 620 | 0 | 78 | 75 | 2 | 2 | 18 | 6600 | 3700 | 0 | 150 | 100 | 96.0 |
| 182 | 590 | 0 | 75 | 75 | 2 | 2 | 21 | 13500 | 7950 | 0 | 75 | 100 | 99.1 |
| 183 | 565 | 0 | 75 | 74 | 2 | 2 | 18 | 4100 | 6400 | 0 | 0 | 100 | 100 |
| 184 | 560 | 0 | 75 | 69 | 2 | 2 | 16 | 7500 | 4900 | 0 | 25 | 100 | 99.5 |
| 185 | 535 | 0 | 75 | 77 | 2 | 2 | 17 | 6700 | 4800 | 0 | 25 | 100 | 99.5 |
| 186 | 600 | 0 | 75 | 75 | 2 | 2 | 16 | 5700 | 4450 | 0 | 25 | 100 | 98.9 |

*Bag counts too low to provide significant efficiency data.

TABLE 18

| Example No. | PRC DATA | | | | | | Priming Time, Seconds | LEUKOCYTE COUNT | | | | LEUKOCYTE EFFICIENCY, % | |
|---|---|---|---|---|---|---|---|---|---|---|---|---|---|
| | Volume of Two Bags, cc | Volume Remaining cc | Hematocrit, % | | Age, Days | | | Bag | | Filtrate | | | |
| | | | #1 | #2 | #1 | #2 | | 1 | 2 | 1 | 2 | 1 | 2 |
| 187 | 557 | 50 | 84 | 78 | 23 | 23 | 19 | 50 | 100 | 0 | 0 | * | * |
| 188 | 551 | 12 | 86 | 76 | 23 | 27 | 23 | 100 | 350 | 0 | 0 | * | 100 |
| 189 | 600 | 124 | 79 | 69 | 23 | 27 | 18 | 150 | 250 | 0 | 0 | * | * |
| 190 | 536 | 86 | 88 | 72 | 23 | 27 | 24 | 150 | 150 | 0 | 0 | * | * |
| 191 | 548 | 0 | 75 | 79 | 23 | 27 | 12 | 50 | 100 | 0 | 0 | * | * |
| 192 | 647 | 57 | 79 | 60 | 23 | 27 | 14 | 50 | 50 | 0 | 0 | * | * |
| 193 | 653 | 0 | 68 | 70 | 35 | 35 | 24 | 150 | 50 | 0 | 0 | * | * |
| 194 | 579 | 0 | 75 | 70 | 31 | 35 | 13 | 100 | 150 | 0 | 0 | * | * |
| 195 | 641 | 0 | 70 | 76 | 31 | 35 | 18 | 50 | 50 | 0 | 0 | * | * |
| 196 | 550 | 0 | 79 | 75 | 31 | 35 | 18 | 50 | 0 | 0 | 0 | * | * |
| 197 | 601 | 375 | 78 | 79 | 35 | 35 | 23 | 100 | 50 | 0 | 0 | * | * |
| 198 | 587 | 0 | 72 | 73 | 35 | 35 | 20 | 150 | 100 | 0 | 0 | * | * |

*Bag counts too low to provide significant efficiency data.

TABLE 19

| Example No. | PRC DATA | | | | | | | LEUKOCYTE COUNT | | | | LEUKOCYTE EFFICIENCY, % | |
|---|---|---|---|---|---|---|---|---|---|---|---|---|---|
| | Volume of Two Bags, cc | Volume Remaining cc | Hematocrit, % | | Age, Days | | Priming Time, Seconds | Bag | | Filtrate | | | |
| | | | #1 | #2 | #1 | #2 | | 1 | 2 | 1 | 2 | 1 | 2 |
| 199 | 537 | 127 | 81 | 78 | 35 | 35 | 34 | 0 | 50 | 0 | 0 | * | * |
| 200 | 576 | 253 | 72 | 76 | 35 | 35 | 23 | 250 | 0 | 0 | 0 | 100 | * |
| 201 | 642 | 239 | 49 | 65 | 35 | 35 | 22 | 0 | 50 | 0 | 0 | * | * |
| 202 | 577 | 289 | 71 | 81 | 35 | 35 | 20 | 50 | 0 | 0 | 0 | * | * |
| 203 | 543 | 0 | 68 | 70 | 35 | 35 | 17 | 0 | 0 | 0 | 0 | * | * |
| 204 | 633 | 278 | 72 | 70 | 35 | 35 | 19 | 0 | 0 | 0 | 0 | * | * |
| 205 | 642 | 0 | 70 | 70 | 25 | 25 | 18 | 150 | 100 | 0 | 0 | * | * |
| 206 | 587 | 39 | 78 | 80 | 25 | 27 | 21 | 0 | 50 | 0 | 0 | * | * |
| 207 | 571 | 106 | 76 | 81 | 27 | 23 | 17 | 50 | 50 | 0 | 0 | * | * |
| 208 | 637 | 0 | 70 | 74 | 26 | 24 | 15 | 50 | 100 | 0 | 0 | * | * |
| 209 | 377** | 19** | 77 | 77 | 27 | 27 | 24 | 100 | — | 0 | 0 | * | * |
| 210 | 529 | 101 | 72 | 85 | 27 | 23 | 20 | 150 | 200 | 0 | 0 | * | * |

*Bag count too low to provide significant efficiency data.
**Did not complete first bag.

I claim:

1. A device for separating one or more substances from a fluid to be administered to a patient, the device comprising a housing including an inlet and an outlet and defining a fluid flow path between the inlet and the outlet and a separating element disposed within the housing across the fluid flow path and including a downstream surface, wherein the inlet communicates with the housing near the bottom of the housing and upstream from the separating element and wherein the housing includes a wall facing the downstream surface of the separating element and defining a plenum and a slot disposed in the wall and communicating between the plenum and the outlet for allowing air in the fluid to separate from the fluid, said outlet being located near the top of the housing.

2. The device of claim 1 wherein the slot is deeper than the plenum.

3. The device of claim 2 wherein the wall includes a plurality of concentric circular grooves which communicate with the slot.

4. The device of claim 3 wherein the slot extends from the bottom to the top of the housing.

5. The device of claim 2 wherein the slot length is 50 to 80% of an inner diameter of the housing, and the slot extends to the top of the housing.

6. The device of claim 5 wherein the slot depth increases towards the top of the housing.

7. The device of claim 2 wherein the housing has a generally circular configuration and the slot extends from the top of the housing along at least a portion of the length of the vertical inner diameter of the housing.

8. The device of claim 1 wherein the slot extends from the bottom to the top of the housing.

9. A method for the depletion of the leukocyte content of blood product comprising passing the blood product through the device of claim 1.

10. A device for separating one or more substances from a fluid to be administered to a patient, the device comprising a generally cylindrical housing including an inlet and an outlet and defining a fluid flow path between the inlet and the outlet and a disc shaped separation element disposed within the housing and having upstream and downstream surfaces, wherein the housing further includes an inlet section facing the upstream surface of the separating element and defining an inlet plenum, the inlet including a ridge extending vertically along the exterior of the inlet section and a first passageway which opens at the top of the inlet ridge, extends through the inlet ridge, and communicates with the inlet plenum at the bottom of the housing, and an outlet section facing the downstream surface of the separating element and defining an outlet plenum and including a slot which is deeper than the outlet plenum and which communicates between the outlet plenum and the outlet, the outlet including a ridge extending vertically along the exterior of the outlet section and a second passageway which opens at the bottom of the outlet ridge, extends through the outlet ridge, and communicates with the slot near the top of the housing.

11. The device of claim 10 wherein the inlet section includes a plurality of concentric circular grooves and an access extending between the inlet passageway and each circular groove, the circular grooves and the access collectively defining the inlet plenum and the inlet plenum having a depth which is greatest at the bottom of the housing near the inlet passageway.

12. The device of claim 10 wherein the outlet section includes a plurality of concentric circular grooves which communicate with the slot and wherein the slot extends from near the bottom of the housing to the top of the housing and has a greater depth at the top of the housing than at the bottom.

13. The device of claim 10 wherein the housing further includes a cylindrical collar disposed about the periphery of the disc shaped separation element, the disc shaped separation element being sealed to the cylindrical collar by an interference fit between them.

14. A method for the depletion of the leukocyte content of blood product comprising passing the blood product through the device of claim 10.

* * * * *